United States Patent
Sahebkar et al.

(10) Patent No.: US 9,987,375 B2
(45) Date of Patent: Jun. 5, 2018

(54) METHOD AND COMPOSITION FOR TREATMENT OF DYSLIPIDEMIA AND OTHER DISEASES

(71) Applicants: Amirhossein Sahebkar, Mashhad (IR); Ali Badiee, Mashhad (IR); Mahmoud Reza Jaafari, Mashhad (IR)

(72) Inventors: Amirhossein Sahebkar, Mashhad (IR); Ali Badiee, Mashhad (IR); Mahmoud Reza Jaafari, Mashhad (IR)

(*) Notice: Subject to any disclaimer, the term of this patent is extended or adjusted under 35 U.S.C. 154(b) by 251 days.

(21) Appl. No.: 14/492,060

(22) Filed: Sep. 21, 2014

(65) Prior Publication Data

US 2015/0147383 A1 May 28, 2015

Related U.S. Application Data

(60) Provisional application No. 61/880,983, filed on Sep. 23, 2013.

(51) Int. Cl.
| | |
|---|---|
| *A61K 38/00* | (2006.01) |
| *A61K 47/48* | (2006.01) |
| *A61K 9/127* | (2006.01) |
| *A61K 47/69* | (2017.01) |

(52) U.S. Cl.
CPC ........ *A61K 47/48823* (2013.01); *A61K 9/127* (2013.01); *A61K 47/6913* (2017.08)

(58) Field of Classification Search
CPC .......... A61K 47/48823; A61K 47/6913; A61K 9/127
See application file for complete search history.

(56) References Cited

U.S. PATENT DOCUMENTS

| | | | | |
|---|---|---|---|---|
| 5,340,587 A * | 8/1994 | Mihalko | ............. | A61K 9/0078 424/45 |
| 5,408,038 A * | 4/1995 | Smith | ................. | C07K 14/775 435/7.1 |
| 5,527,528 A * | 6/1996 | Allen | ................... | A61K 9/1271 424/178.1 |
| 5,945,122 A * | 8/1999 | Abra | .................... | A61K 9/1271 264/4.1 |
| 2003/0235611 A1* | 12/2003 | Ehringer | ............ | A61K 31/7076 424/450 |
| 2008/0213346 A1* | 9/2008 | Oh | .......................... | A61K 8/14 424/450 |

OTHER PUBLICATIONS

Canovi, Mara (Biomaterials 32(23), 5489-5497, 2011).*
Markoutsa, Eleni (European Journal of Pharmaceutics and Biopharmaceutics 81(1), 49-56, 2012).*
Scholfield (J. Am. Oil. Chem. Soc. 58 (10) 889-892, 1981).*
Sahebkar, Amirhossein (Colloids and Surfaces, B: Biointerfaces 129, 71-78, 2015).*
Sahebkar et al. Apolipoprotein B-100-targeted negatively charged nanoliposomes for the treatment of dyslipidemia. Colloids and Surfaces B: Biointerfaces, 2015. vol. 128, pp. 71-78.*

* cited by examiner

*Primary Examiner* — Marcela M Cordero Garcia
(74) *Attorney, Agent, or Firm* — NovoTechIP International PLLC

(57) ABSTRACT

Anionic liposomes and apolipoprotein B-100 targeted immunoliposomes as therapeutic agents for dyslipidemia and related diseases, and compositions and methods for preparing same.

12 Claims, 24 Drawing Sheets

METHOD AND COMPOSITION FOR TREATMENT OF DYSLIPIDEMIA AND OTHER DISEASES

CROSS REFERENCE TO RELATED APPLICATION

The present invention claims priority from U.S. Provisional Patent Application Ser. No. 61/880,983, filed Sep. 23, 2013, entitled "Application of anionic liposomes and apolipoprotein B-100 targeted immunoliposomes as therapeutic agents for dyslipidemia," the subject matter of which is incorporated by reference herein in its entirety.

SPONSORSHIP STATEMENT

This application has been sponsored by the Iranian Nanotechnology Initiative Council, which does not have any rights in this application.

TECHNICAL FIELD

The present invention relates to the application of a novel composition useful for the treatment of coronary artery disease (CAD) and a method for preparing the composition, including compositions generally having targeted imunoliposome conjugated with Apolipoprotein B-100 (apo B-100) with an average diameter of about 100-150 nanometers and method for preparing thereof.

BACKGROUND OF THE INVENTION

Coronary artery disease (CAD) is the leading cause of mortality worldwide. Annually, CAD imposes significant financial burdens and casualties on healthcare systems across the world. Therefore, the current focus of many health policy making authorities is to find effective ways for the optimal prevention and management of CAD.

Among the most important modifiable risk factors for CAD is dyslipidemia, which is characterized by elevated levels of low-density lipoprotein cholesterol (LDL-C), and diminished concentrations of high-density lipoprotein cholesterol (HDL-C). Extensive evidence, including findings of the several landmark trials, has confirmed the beneficial impact of LDL reduction in both primary and secondary prevention of cardiovascular disorders.

According to recent guidelines, optimal levels for serum LDL-C have been suggested to be around 60-70 mg/dL. However, statin—as the most potent LDL-lowering class of drugs—is only able to reduce serum LDL in around 30-50% of cases. Additionally, such a reduction would be achieved with aggressive therapy, which may itself predispose the patient to adverse events, such as myopathies and hepatotoxicity. In recent decades, there has been an increasing focus on boosting HDL concentrations to fulfill the residual cardiovascular risk, which is not compensated by LDL reduction. In addition to their inadequate potency for decreasing serum LDL to the optimal level, statins also have a limited effect on serum HDL-C concentrations.

As is known in the art, liposomes are artificial phospholipid bilayers, which have long been used as carriers to enhance the potency and reduce the toxicity of drugs. These constructs have generated great interest for biomedical purposes due to their biocompatibility, biodegradability, safety and lack of immunogenicity. Nanoliposomes are known to have a short half-life in the circulation. Biodistribution studies have shown that within a few hours of intravenous injection, nanoliposomes are efficiently taken up by hepatic tissue. This uptake has been shown to be performed through receptor mediated endocytosis, a process which normally occurs for the clearance of LDL from circulation.

On the other hand, there is also evidence indicating the coalescence of liposomes containing 75-100% mol anionic phospholipids with LDL, and the uptake of resulting complex via either LDL receptors or macrophages. In addition, liposomes have been shown to undergo vast lipid exchange with plasma lipoproteins, and through these interactions, promote reverse cholesterol transport from peripheral tissues to liver. In spite of these promising mechanisms, the potential of liposomes as anti-dyslipidemic agents has not been well clarified.

Apo lipoprotein B is a large glycoprotein that serves an indispensable role in the assembly and secretion of lipids, and in the transport and receptor-mediated uptake and delivery of distinct classes of lipoproteins. The importance of Apo lipoprotein B spans a variety of functions, from the absorption and processing of dietary lipids to the regulation of circulating lipoprotein levels.

ApoB-100 is the major protein component of LDL and contains the domain required for interaction of this lipoprotein species with the LDL receptor. Therefore, the targeting of liposomes against Apo B-100 is expected to enhance the effects of liposomal formulations on the LDL fraction, and result in greater reduction rates.

The general use of liposomes for the reduction of LDL is known. However, the prior art known to Applicant fails to disclose that the antibody anti-apoB100 can be used in combination with nano liposomes. This particular aspect is absent in the prior art.

The present invention found that the effect of nanoliposomes with different phospholipid composition, Tm and charge on serum levels of lipoproteins. In connection with the present invention, a study was also undertaken to evaluate the impact of targeting liposomes to LDL via coupling to apolipoprotein B-100 (apo B-100) monoclonal antibodies. A proper anionic-to-neutral phospholipid ratio for preparing the said liposomal composition is set forth herein. The objects and features of the present invention, will become apparent in the detailed description of the invention set forth below.

There is, therefore, a present need for such efficacious treatments for coronary artery diseases, as well as related treatments concerning ameliorating the negative effects of bad LDL and other cholesterol levels.

These and many other objects are met in various embodiments of the present invention, offering significant advantages over the known prior art and consequent benefits to all mankind.

SUMMARY OF THE INVENTION

In one embodiment of the present invention, the present invention evaluated the anti-dyslipidemic effects of nanoliposomes with different phospholipid composition Another embodiment of the present invention is directed to cholesterol-free nanoliposomal formulations containing 75% anionic phospholipid (PG) introduced as safe, effective, rapid acting, inexpensive, biocompatible and biodegradable anti-dyslipidemic agents.

In a further embodiment of the present invention, the present invention and surrounding study evaluated the impact of targeting liposomes to the reduction of LDL via coupling to apolipoprotein B-100 (apo B-100) monoclonal antibodies.

In still another embodiment of the present invention, targeting of liposomes against Apo B-100 as an effective liposomal composition was performed, and the reduction of all lipid profile parameters (LDL-C, HDL-C, total cholesterol and triglycerides) was evaluated.

In a still further embodiment of the present invention, the targeting of hydrogenated soy phosphatidylcholine/1,2-distearoyl-sn-glycero-3-phosphoglycerol (HSPC/DSPG) and soy phosphatidylcholine/egg phosphatidylglycerol (SPC/EPG) liposomes against apo B-100 components of LDL increased, and this increased the LDL-lowering effects. In this instance, reduced LDL-C levels were sustained for at least hours. Atherogenic indices (either calculated as LDL-C/HDL-C or log (triglycerides/HDL-C)) were also effectively reduced following HSPC/DSPG and SPC/EPG injections, demonstrating the efficacy of the present invention, as set forth and described further hereinbelow.

In another embodiment, empty, cholesterol-free nanoliposomal and nanoimmunoliposomal formulations containing 70-80% anionic phospholipid (PG) were determined as possible safe, effective, rapid acting, inexpensive, biocompatible and biodegradable anti-dyslipidemic agents, meriting further research and study.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying DRAWINGS, where like reference numerals designate like structural and other elements, in which:

Figure 16:
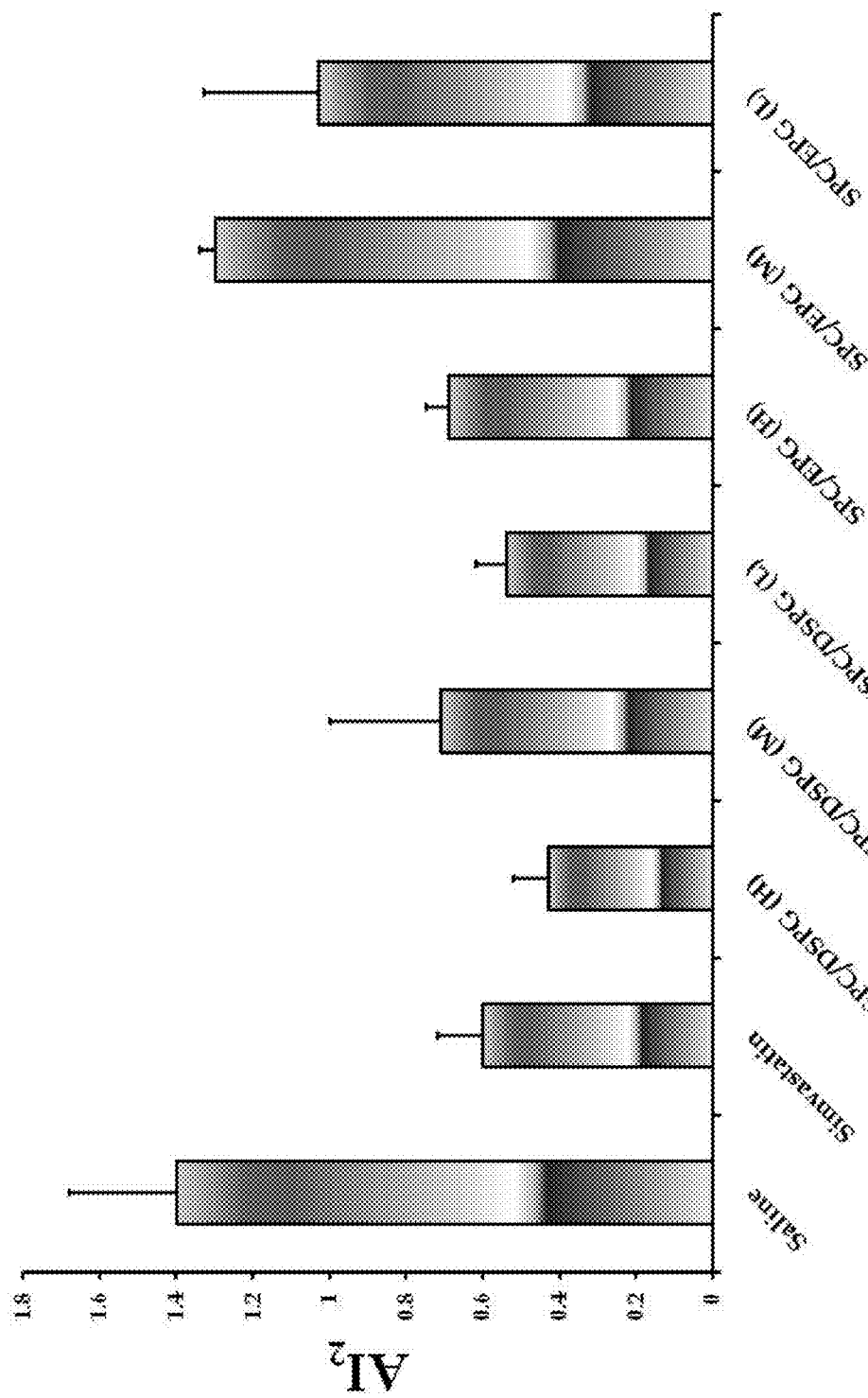
Figure 17:
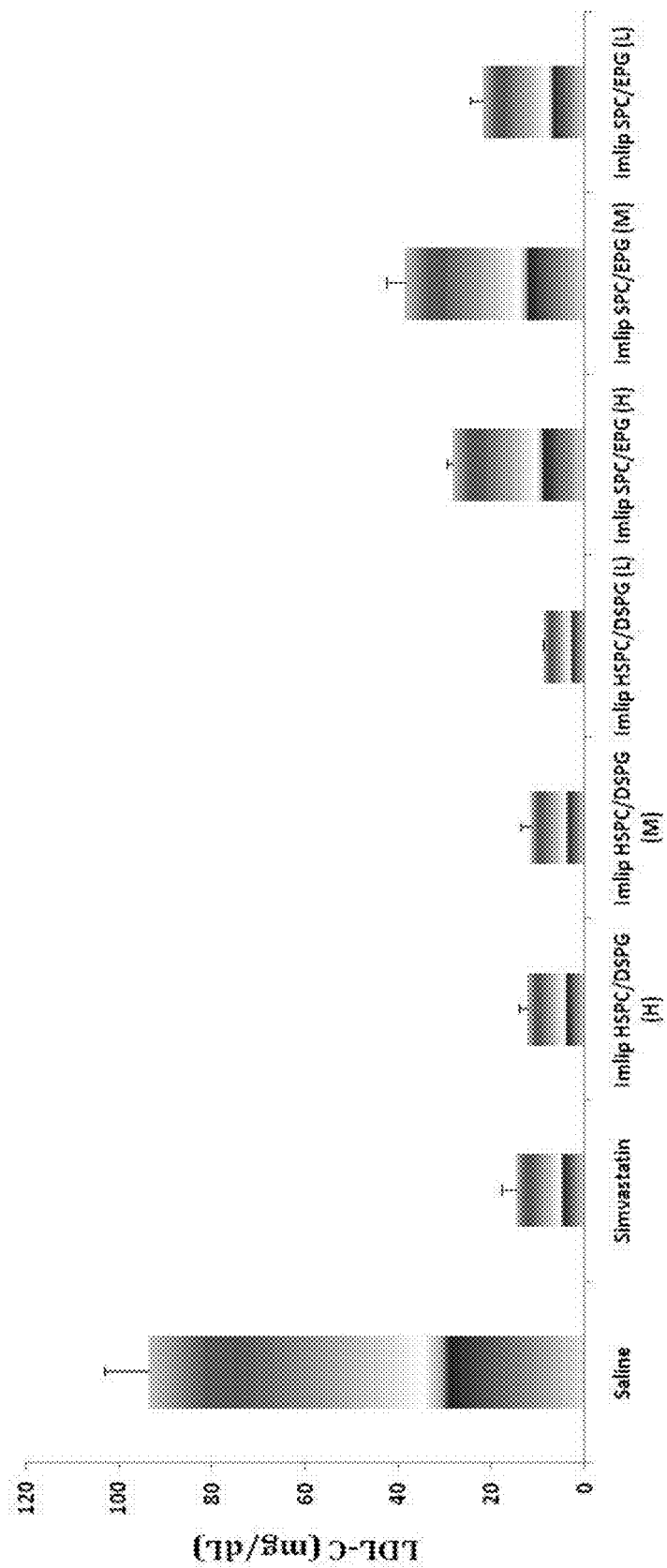
Figure 18:
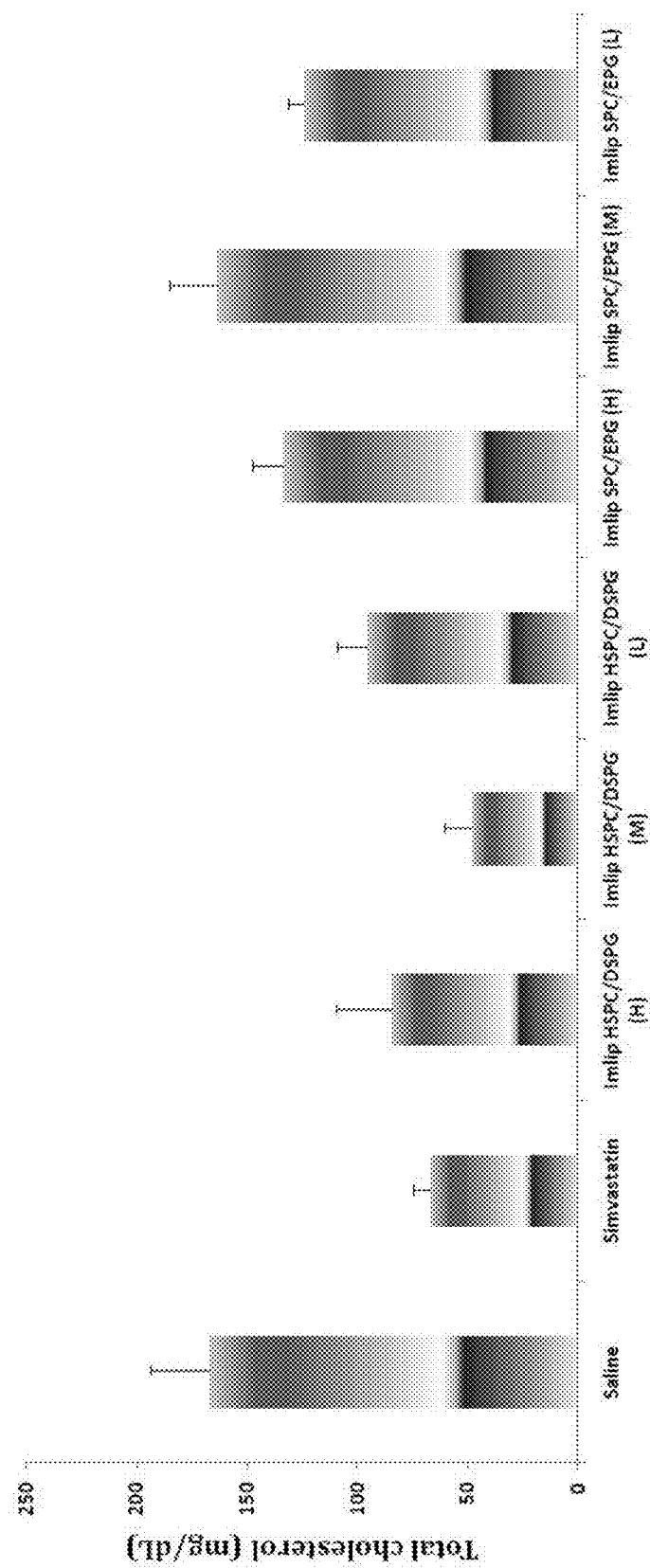
Figure 19:
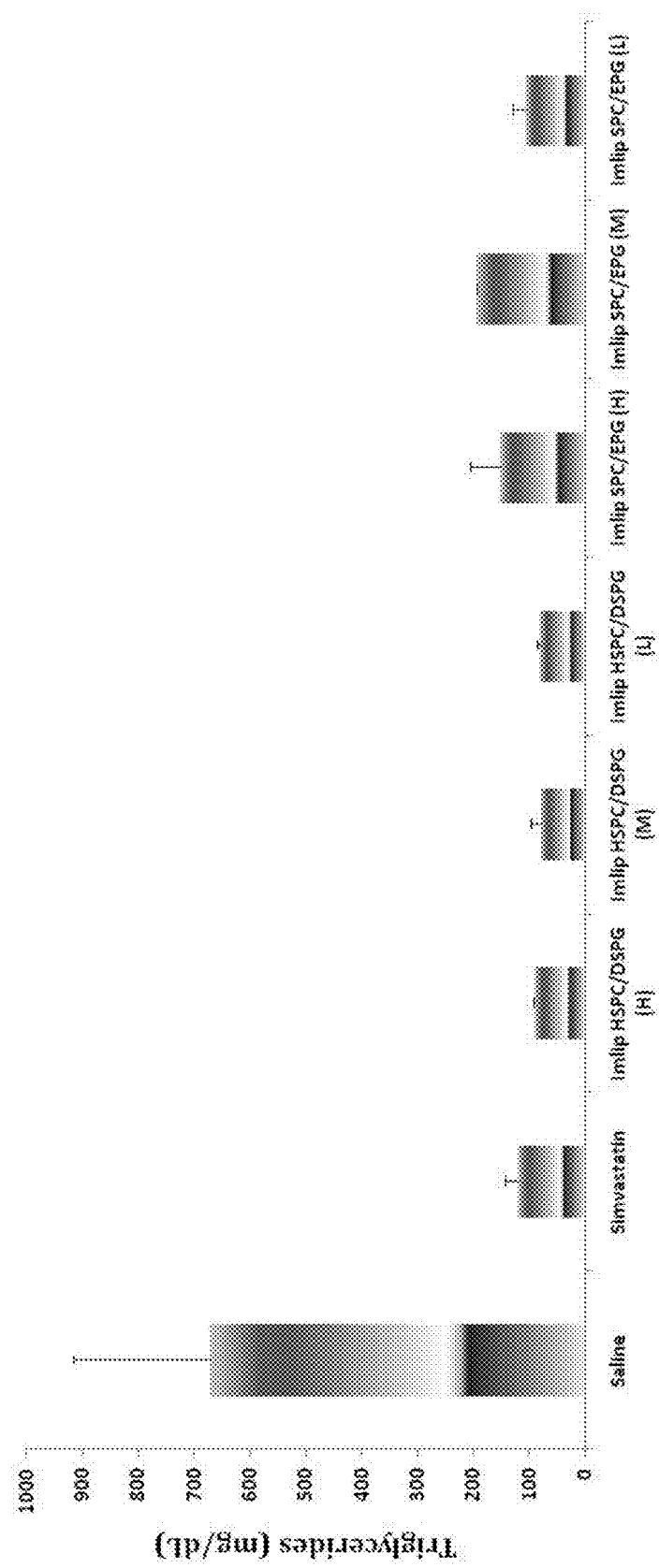
Figure 20:
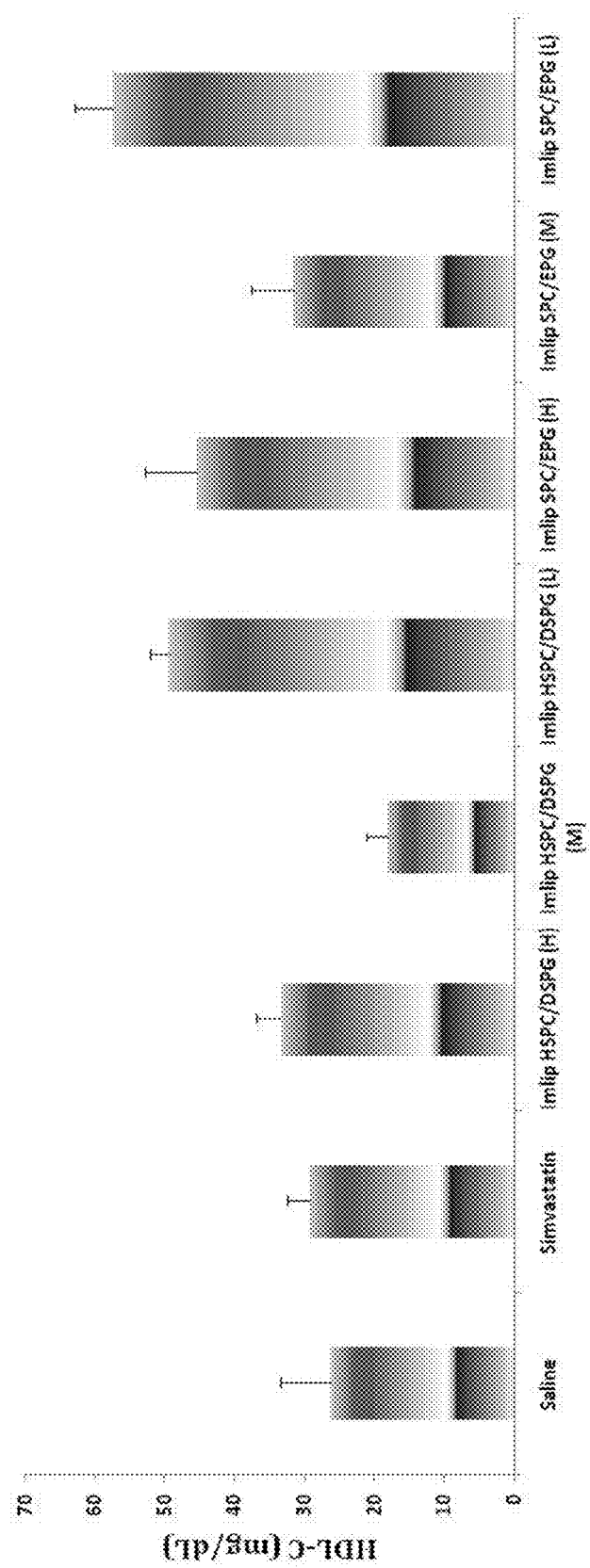
Figure 21:
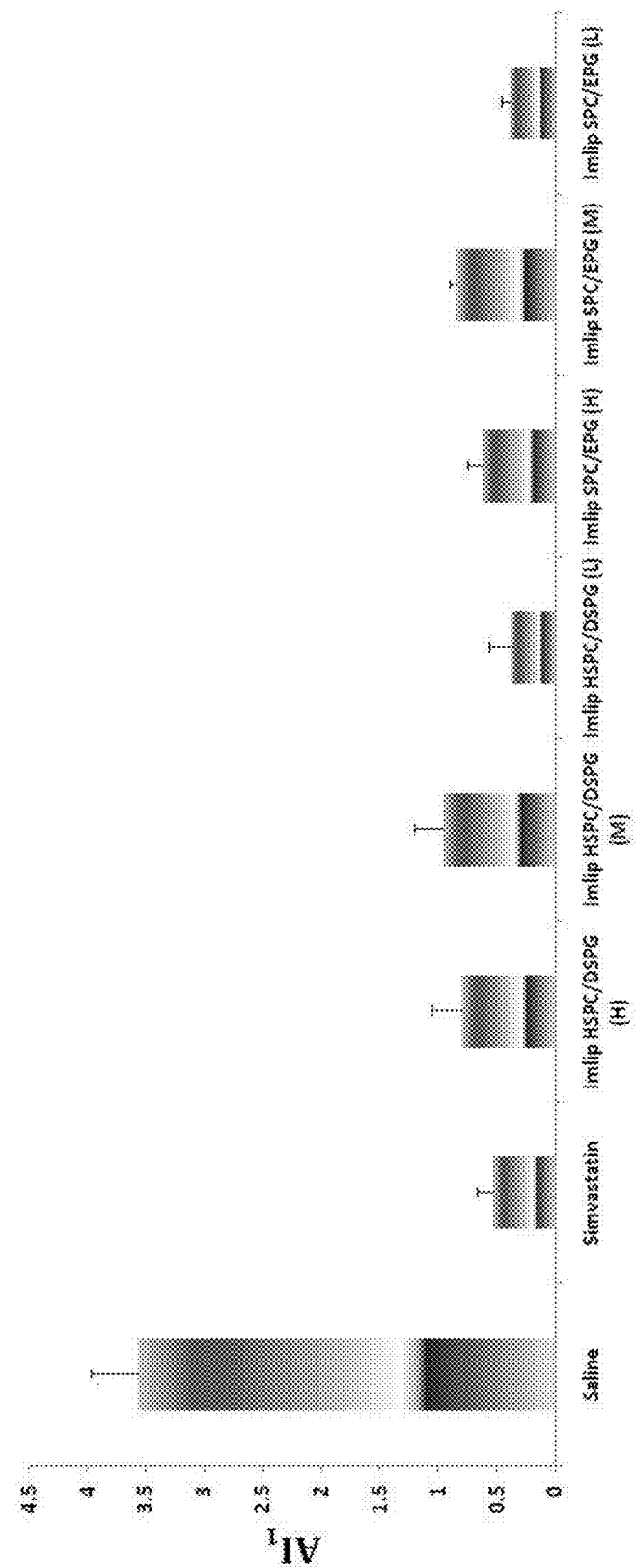
Figure 22:
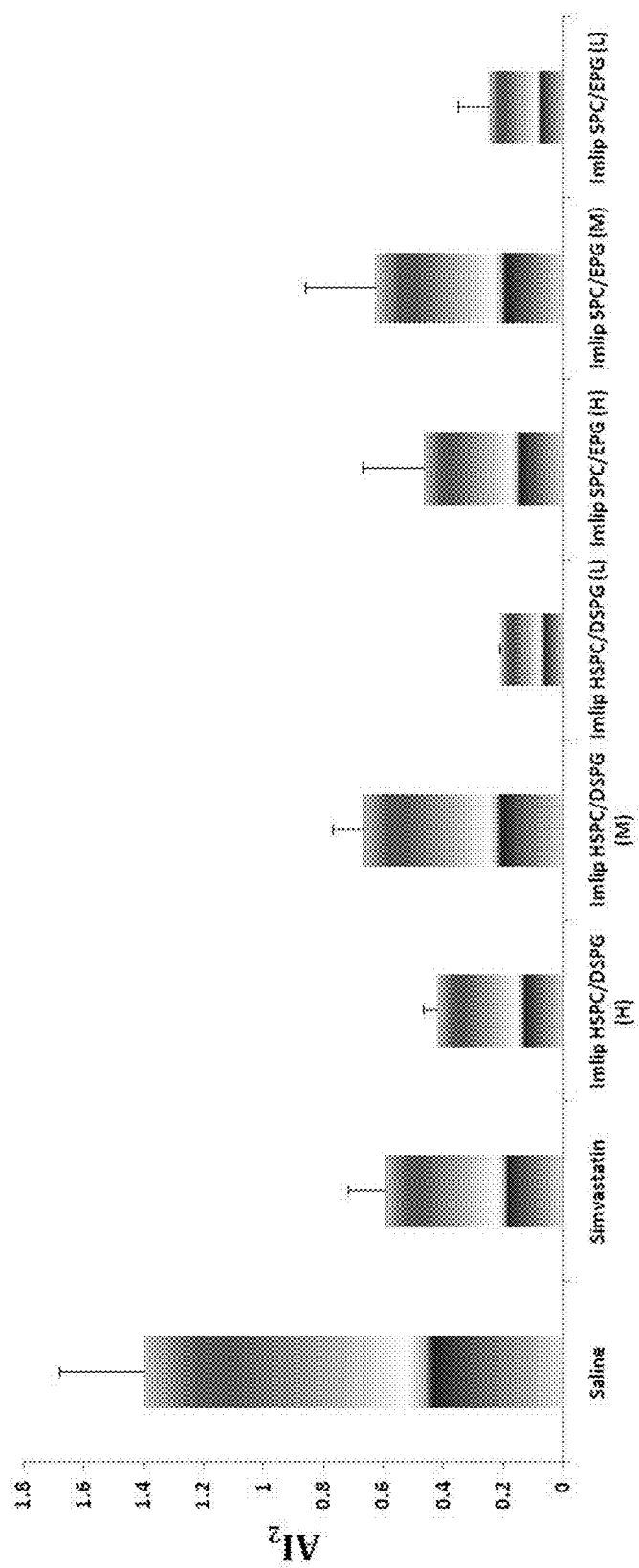
Figure 23:
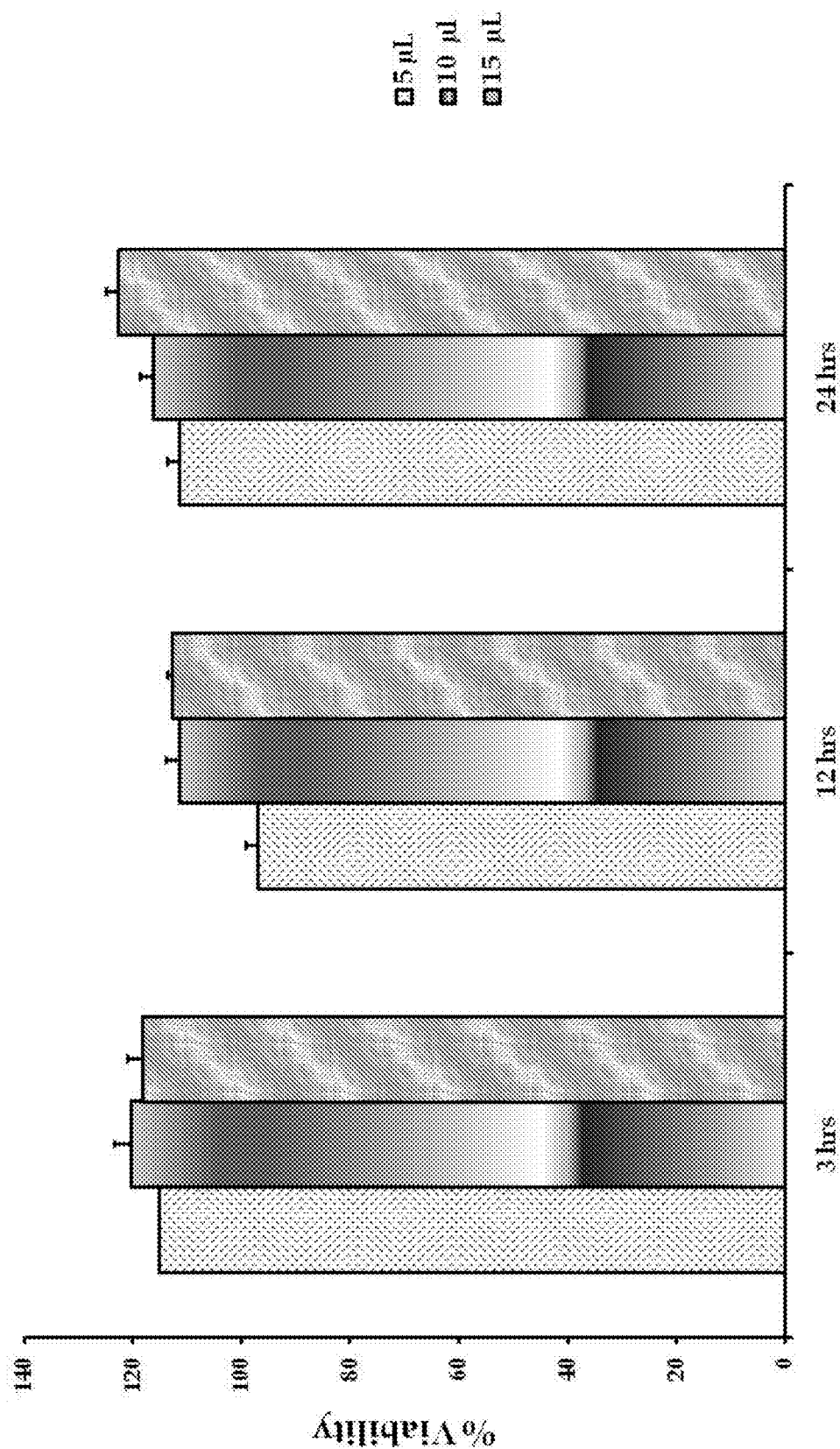
Figure 24:
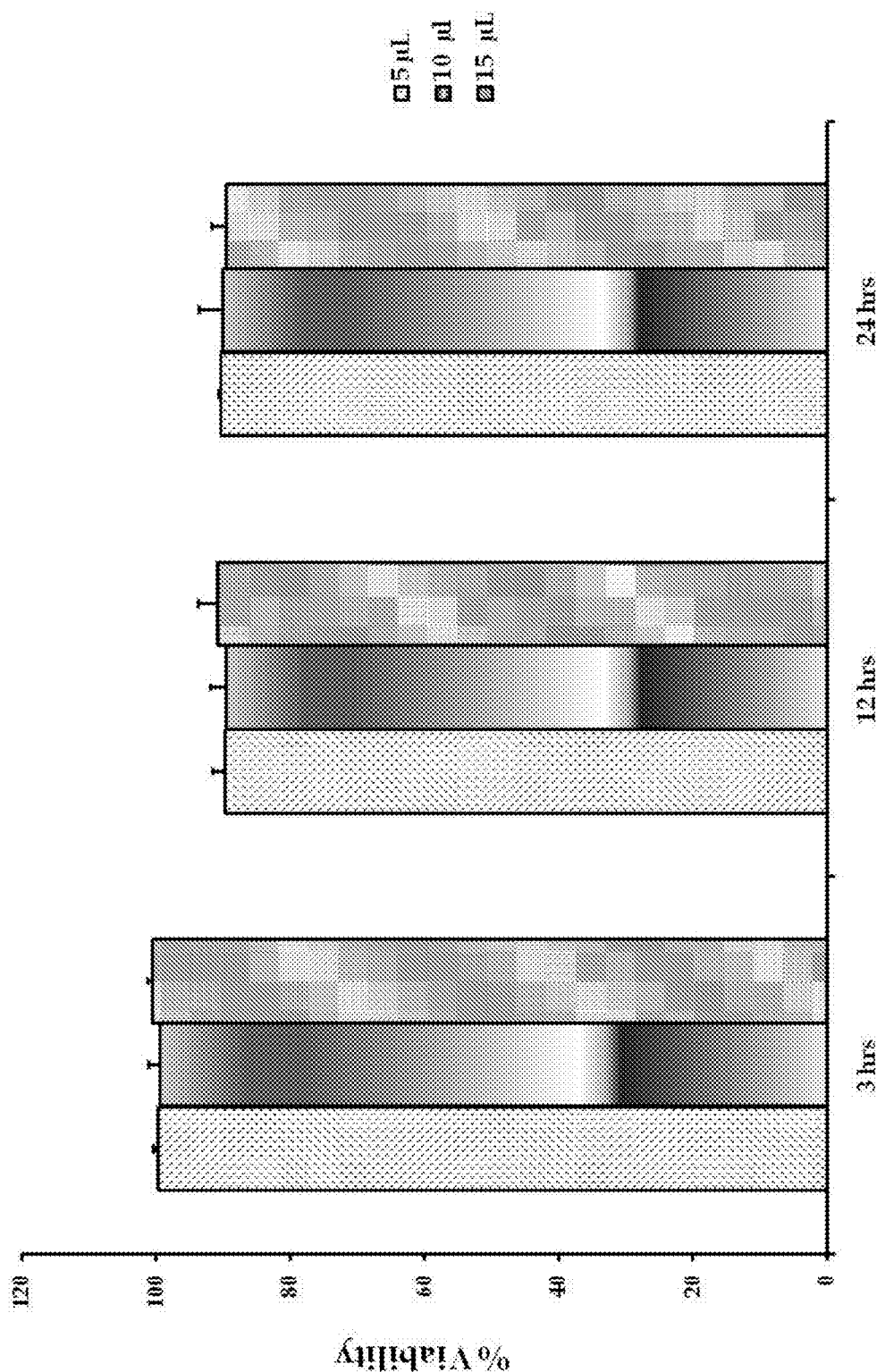

FIG. 16 illustrates in-vivo effects of different doses of anionic liposomes on $AI_2$ calculated as log (triglycerides/HDL-C) pursuant to the teachings of the present invention. AI: atherogenic index. H: high concentration (200 μmole/kg); M: medium concentration (100 μmole/kg); L: low concentration (50 μmole/kg). Values are expressed as mean±SEM;

FIG. 17 illustrates in-vivo effects of different doses of Apo B-100 targeted immunoliposomes on serum LDL-C concentrations pursuant to additional teachings of the present invention. H: high concentration (200 μmole/kg); M: medium concentration (100 μmole/kg); L: low concentration (50 μmole/kg). Values are again expressed as mean±SEM;

FIG. 18 illustrates in-vivo effects of different doses of apo B-100 targeted immunoliposomes on serum total cholesterol concentrations pursuant to the teachings of the present invention. H: high concentration (200 μmole/kg); M: medium concentration (100 μmole/kg); L: low concentration (50 μmole/kg). Values are here also expressed as mean±SEM;

FIG. 19 illustrates in-vivo effects of different doses of apo B-100 targeted immunoliposomes on serum triglycerides concentrations pursuant to further teachings of the present invention. H: high concentration (200 μmole/kg); M: medium concentration (100 μmole/kg); L: low concentration (50 μmole/kg), and the values are expressed as mean±SEM;

FIG. 20 illustrates in-vivo effects of different doses of Apo B-100 targeted immunoliposomes on HDL-C concentrations pursuant to further teachings of the present invention. H: high concentration (200 μmole/kg); M: medium concentration (100 μmole/kg); L: low concentration (50 μmole/kg). Values are again expressed as mean±SEM;

FIG. 21 illustrates in-vivo effects of different doses of apo B-100 targeted immunoliposomes on $AI_1$ calculated as LDL-C/HDL-C pursuant to the teachings of the instant invention. AI: atherogenic index. H: high concentration (200 μmole/kg); M: medium concentration (100 μmole/kg); L: low concentration (50 μmole/kg). Values are expressed as mean±SEM;

FIG. 22 illustrates in-vivo effects of different doses of apo B-100 targeted immunoliposomes on $AI_2$ calculated as log (triglycerides/HDL-C) pursuant to the teachings of the present invention. AI: atherogenic index. H: high concentration (200 μmole/kg); M: medium concentration (100 μmole/kg); L: low concentration (50 μmole/kg). Values are expressed as mean±SEM;

FIG. 23 illustrates dose- and time-dependent evaluation of the viability of J774.A1 macrophages in the presence of HSPC/DSPG liposomes pursuant to further teachings of the present invention. Values are expressed as mean±SEM; and FIG. 24 illustrates dose- and time-dependent evaluation of the viability of J774.A1 macrophages in the presence of SPC/EPG liposomes pursuant to the various teachings of the present invention. Values are expressed as mean±SEM.

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The materials and substances used in practicing the principles of the present invention include: hydrogenated soy phosphatidylcholine (HSPC), soy phosphatidylcholine (SPC), egg phosphatidylglycerol (EPG), 1-palmitoyl-2-oleoyl-sn-glycero-3-phosphocholine (POPC), 1,2-dimiristoyl-sn-glycero-3-phosphoglycerol (DMPG), 1,2-distearoyl-sn-glycero-3-phosphoglycerol (DSPG), fluorescent dye 1,1-dioctadecyl-3,3,3',3'-tetramethylindocarbocyanine perchlorate (DiI), Tyloxapol, simvastatin and Alamar Blue.

Figure 1:
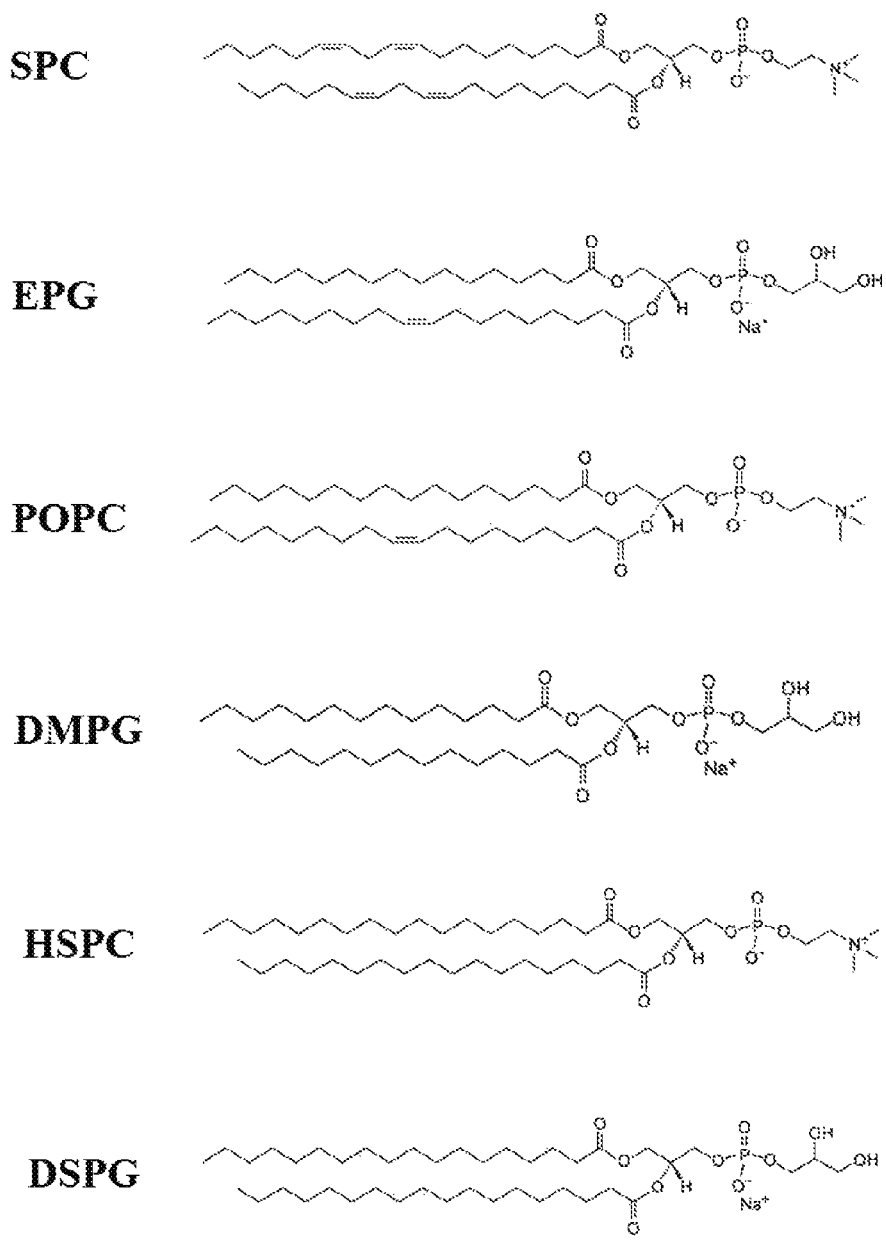
FIG. 1 generally illustrates various chemical structures of phospholipids used for the preparation of liposomes.

Conventional liposomes were prepared from different phospholipids (HSPC, SPC, POPC, DMPG, EPG or DMPG) by the method of dried lipid-film hydration plus extrusion. Phospholipids were different in their liquid crystalline transition temperature ($T_m$) and charge, as illustrated in FIG. 1 of the DRAWINGS, showing various representative, exemplary structures of phospholipids used in the preparation of the liposomes pursuant to the principles of the present invention.

Briefly, three sets of liposomal formulations, as set forth in TABLE 1 hereinbelow, were prepared with low (soy phosphatidylcholine, SPC; $T_m$<0° C.), medium (palmitoyl-oleoyl-phosphatidylcholine, POPC; $T_m$=0° C.) and high (hydrogenated soy phosphatidylcholine, HSPC; $T_m$=55° C.) Tm values with (HSPC/chol; POPC/chol; SPC/chol) and without cholesterol (HSPC; POPC; SPC) and anionic phosphatidyl glycerol (HSPC/DSPG; POPC/DMPG; SPC/EPG) at a final lipid concentration of 20 mM. The anionic formulations were cholesterol-free and contained an anionic phospholipid amounting 75% of total phospholipid content. Fluorescence labeling of liposomes was performed using DiI (~0.2 mol % of phospholipid). After vacuum and freeze drying, the obtained thin lipid film was hydrated with histidine (10 mM)/sucrose (10%) buffer (pH 6.5). The resultant multilamellar dispersions were reduced in size lamellarity by vortexing, sonication and extrusion through 200 nm (5 cycles) and 100 nm (11 cycles) polycarbonate membranes using a thermobarrel extruder, as is understood in the art.

TABLE 1

Particle size distribution, zeta potential and polydispersity of liposomal formulations.

| Formulation | Molar ratio | Z-Average (d · nm) | PDI | Zeta potential (mV) |
|---|---|---|---|---|
| HSPC | — | 129.6 ± 2.76 | 0.175 ± 0.11 | −10.2 ± 4.92 |
| HSPC/Chol | 5/1 | 121.7 ± 26.52 | 0.172 ± 0.12 | −9.76 ± 8.19 |
| HSPC/DSPG | 1/3 | 108 ± 1.01 | 0.44 ± 0.01 | −50.9 ± 14.50 |
| SPC | — | 81.64 ± 3.57 | 0.295 ± 0.04 | −10.1 ± 0.57 |
| SPC/Chol | 5/1 | 82.40 ± 1.75 | 0.26 ± 0.03 | −11.30 ± 1.70 |
| SPC/EPG | 1/3 | 95.31 ± 35.77 | 0.20 ± 0.02 | −49.7 ± 15.8 |
| POPC | — | 119.30 ± 15.56 | 0.18 ± 0.02 | −10.02 ± 2.65 |
| POPC/Chol | 5/1 | 121.98 ± 31.28 | 0.17 ± 0.10 | −9.56 ± 0.11 |
| POPC/DMPG | 1/3 | 98.97 ± 7.96 | 0.25 ± 0.17 | −49.55 ± 3.23 |

TABLE 1-continued

Particle size distribution, zeta potential and polydispersity of liposomal formulations.

| Formulation | Molar ratio | Z-Average (d · nm) | PDI | Zeta potential (mV) |
|---|---|---|---|---|
| Apo B-100 targeted immunoliposomes | | | | |
| HSPC/DSPG | 1/3 | 99.03 ± 0.82 | 0.13 ± 0.007 | −23.70 ± 0.71 |
| SPC/EPG | 1/3 | 148.13 ± 4.68 | 0.52 ± 0.01 | −39.4 ± 0.77 |

PDI: poly dispersity index. Values are expressed as mean ± SD, n = 3.

Characterization of the Liposomes

The particle diameter of each sample, together with its polydispersity index, was measured in triplicate using a Dynamic Light Scattering Instrument. The zeta potential of liposomes was determined on the same machine using the zeta potential mode as the average of 20 measurements.

Prepared liposomal formulations had a diameter around 100 nm, with variances between about 80 to about 150 nm, and about 80 to about 120 nm. Overall, the formulations were very homogenous and had a polydispersity index of <0.3. Zeta potential of prepared liposomes ranged between −9.56 (for HSPC/chol) to −50.90 (for HSPC/DSPG), as shown in TABLE 1.

Preparation of Immunoliposomes

In order to conjugate the antibodies to the liposomes, Apo B-100 monoclonal antibody (4.5 mg/mL) was mixed with a heterobifunctional reagent SPDP (6.25 mg/ml; SPDP/mAb molar ratio=10:1) and incubated for 30 min at room temperature to prepare pyridyldithiopropionatedIgG (PDP-IgG), where SPDP includes (3-(2-pyridyldithio) propionic acid N-hydroxysuccinimide ester and PDP-IpG includes Immobilized pH gradient. The mixture was passed immediately through a PD-10 column equilibrated with acetate buffer (0.1M NaCl, 100 mM sodium acetate, pH 4.5) to separate PDP-IgG from excess SPDP. Fractions containing PDP-IgG conjugates (assessed by absorbance in 280 nm) were pooled and reduced with 50 Mm dithiothreitol (DTT) to produce thiolated-IgG (IgG-SH). The IgG-SH was separated from excess DTT by a PD-10 column equilibrated with HEPES buffer. The degree of PDP substitution on the PDP-IgG was determined by measuring the release of 2-thiopyridone ($\epsilon 343=8300M-1$ cm−1) at 343 nm after reduction of the PDP-IgG with DTT. The IgG-SH was mixed immediately with Mpeg2000-DSPE-maleimide micelles (1 mM; micelle/mAb molar ratio=10:1). Resulting micelle-IgG complexes were then mixed with liposomes at 1:1000 molar ratio, and incubated for an hour at 60° C.

Phospholipid Assay

The phospholipid concentration of formulations were determined according to Bartlette test.21. Briefly, liposomal formulations (80±50 µmoles of phosphate containing lipid) were added into disposable borosilicate glass tubes. Then, 0.4 mL of $NH_2SO_4$ was added to each tube. In the fume hood, the sample was digested at 195-210° C. for 60 minutes using a hot-plate apparatus. The tubes were then cooled for about 10 minutes at room temperature. Afterwards, 0.1 mL of 10% $H_2O_2$ was added to each sample and tubes were again heated for 10 minutes at 190-210° C. After cooling the tubes for about 10 minutes, 4.7 ml of molybdate reagent and 0.5 ml of 10% ascorbic acid were added to each tube and vortexed immediately for 10 seconds. Samples were then heated at 100° C. for 10 to 20 minutes, quickly cooled and finally were measured for optical density at 800 nm. The phospholipid concentration of samples was calculated according to the phosphate standard curve.

Liposome Uptake by Macrophages

J774.A1 macrophages were seeded in 12-well tissue culture plates at 3.0×105 cells/well in RPMI 1640 supplemented with 10% fetal calf serum and antibiotics (100 U/mL penicillin and 100 µg/mL streptomycin). Cells were incubated with different liposomal preparations (final phospholipid concentration in each well was set at 0.1 mM). After 3, 10 and 24 hours of incubation, cells were washed with cold phosphate buffered saline (PBS) and then lysed using 1% Triton X-100. Flow cytometric analyses were performed on the obtained lysate. For each sample, the percentage of stained events together with mean fluorescence intensity was determined.

For comparison between the uptake rates of HSPC/DSPG and SPC/EPG, liposomes with their corresponding immunoliposomes, treatment of J774.A1 cells were performed with two different doses of each liposome and immunoliposome i.d. final phospholipid concentrations were set at 0.1 and 0.2 mM.

Macrophage Uptake Assay

Figure 2:
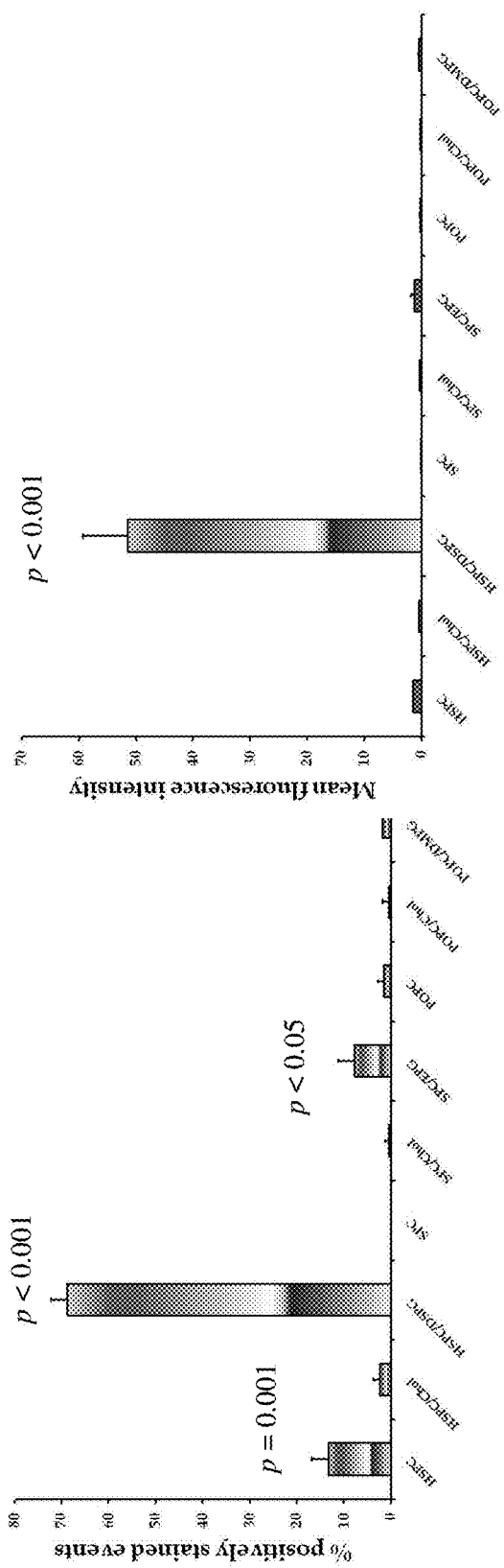
FIG. 2 illustrates a comparison of liposomal formulations in terms of uptake rate by J774.A1 macrophages following 3 hours of incubation pursuant to the teachings of the present invention. The results are shown as % positively stained events (left) and mean fluorescence intensity (right) according to flow cytometric data. Values are expressed as mean±SEM, n=3.
Figure 3:
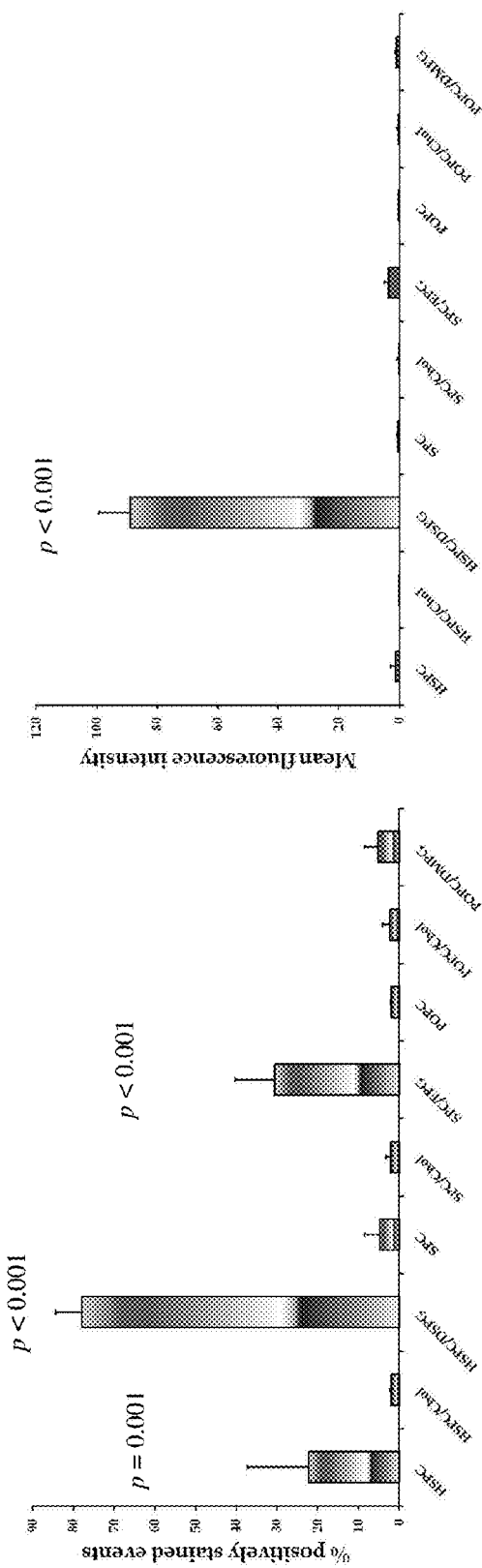
FIG. 3 illustrates a comparison of liposomal formulations in terms of uptake rate by J774.A1 macrophages, as set forth in FIG. 2, but following 10 hours of incubation pursuant to the teachings of the present invention. The results are also shown as % positively stained events (left) and mean fluorescence intensity (right) according to flow cytometric data. Values are also expressed as mean±SEM, n=3.
Figure 4:
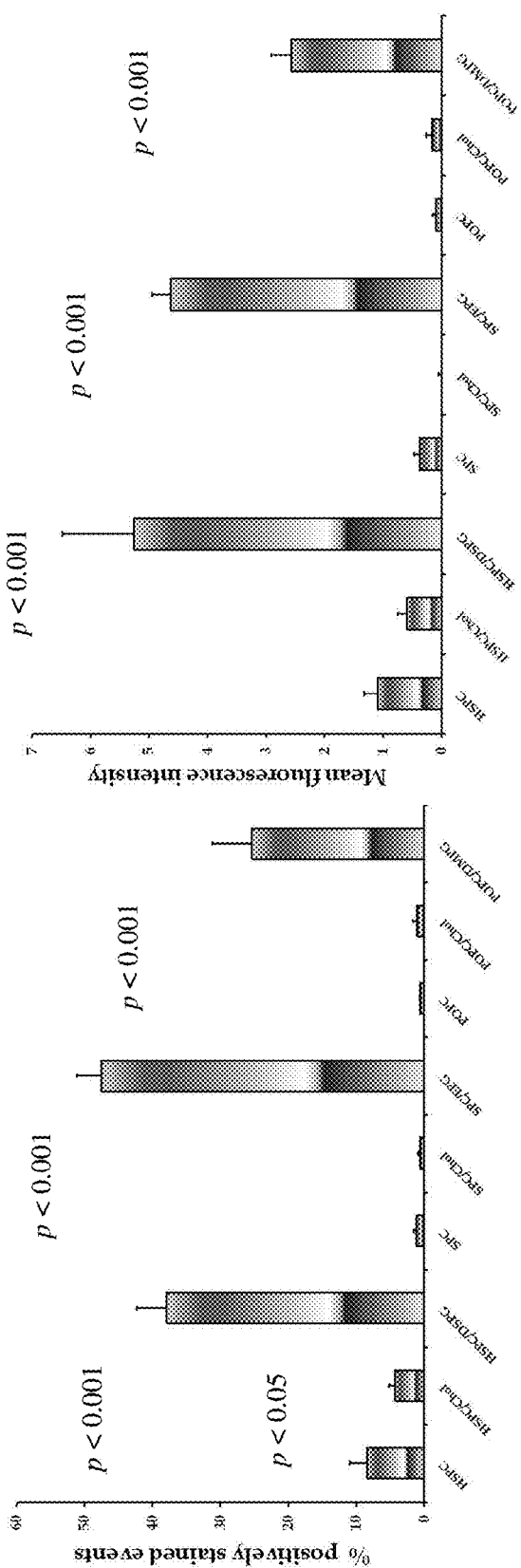
FIG. 4 shows a comparison of liposomal formulations in terms of uptake rate by J774.A1 macrophages, as set forth in FIGS. 2 and 3 hereinabove, but following 24 hours of incubation pursuant to the teachings of the present invention. The results are shown as % positively stained events (left) and mean fluorescence intensity (right) according to flow cytometric data, and the values are expressed as mean±SEM, with n=3.

Percentage of positively-stained events along with the mean fluorescence intensity was used as markers of liposome uptake by J774.A1 macrophages. After 3 and 10 hours of incubation, remarkable uptake rates were only observed for the HSPC/DSPG formulation. However, at the 24 hour time point, all anionic preparations (HSPC/DSPG, SPC/EPG and POPC/DMPG) were markedly uptaken by macrophages. Higher uptake of anionic formulations was consistent using either the mean fluorescence intensity or % positive events as marker, as illustrated and described in more detail in the charts set forth in FIG. 2, FIG. 3 and FIG. 4 of the DRAWINGS, respectively.

Figure 5:
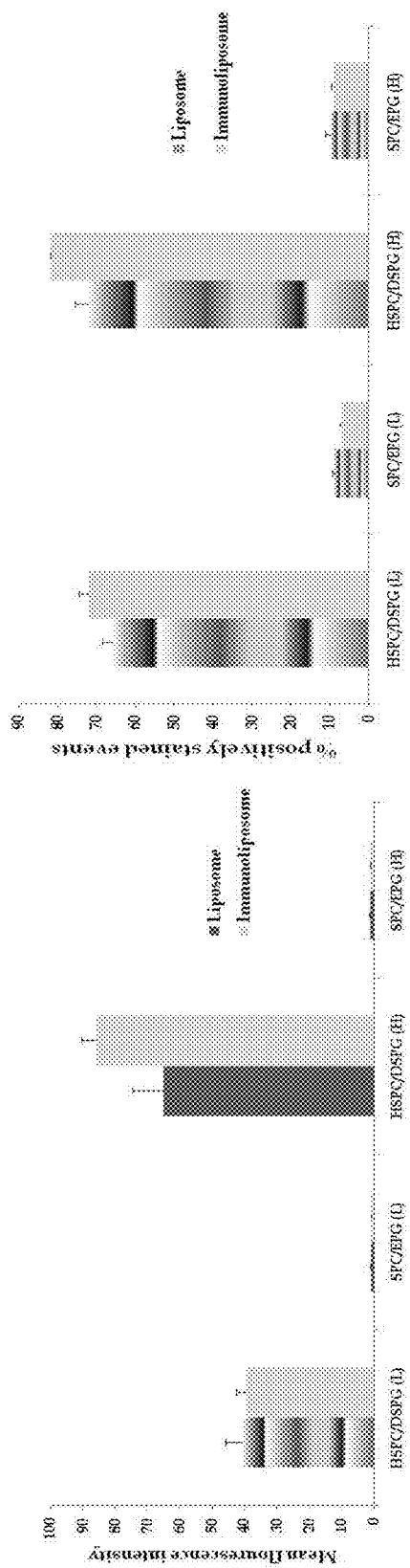
FIG. 5 shows the comparison of liposomal and immunoliposomal formulations in terms of uptake rate by J774.A1 macrophages following 3 hours of incubation pursuant to the teachings of the present invention. The results are shown as % positively stained events (left) and mean fluorescence intensity (right) according to flow cytometric data. H: high dose (final phospholipid concentration in each well was set at 0.1 mM); L (final phospholipid concentration in each well was set at 0.2 mM). Values are expressed as mean±SEM, n=3.
Figure 6:
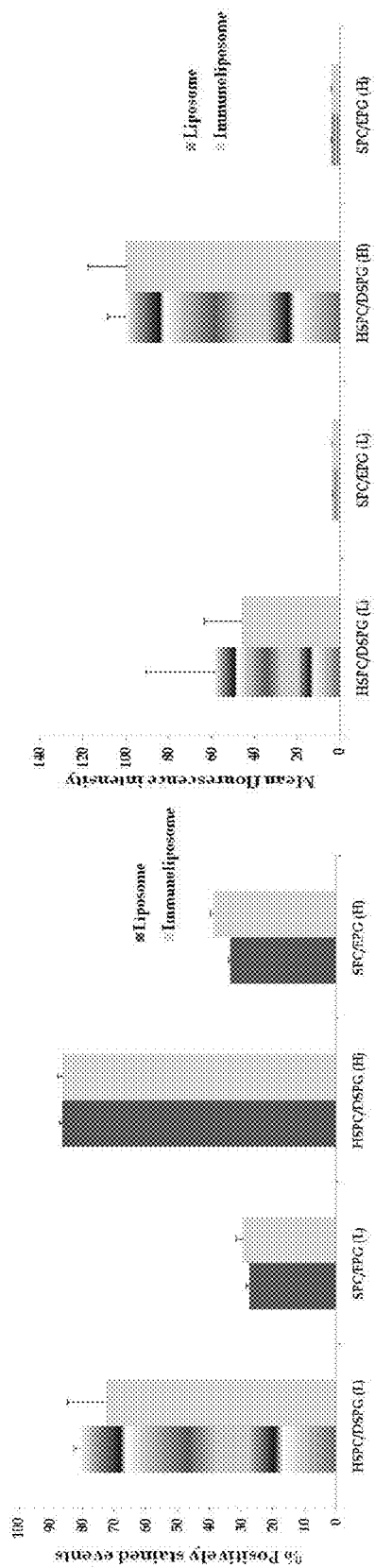
FIG. 6 shows a comparison of liposomal and immunoliposomal formulations in terms of uptake rate by J774.A1 macrophages, as set forth hereinabove in FIG. 5, but following 10 hours of incubation also pursuant to additional teachings of the present invention. The results are shown as % positively stained events (left) and mean fluorescence intensity (right) according to flow cytometric data. H: high dose (final phospholipid concentration in each well was set at 0.1 mM); L (final phospholipid concentration in each well was set at 0.2 mM). Values are expressed as mean±SEM, with n=3.
Figure 7:
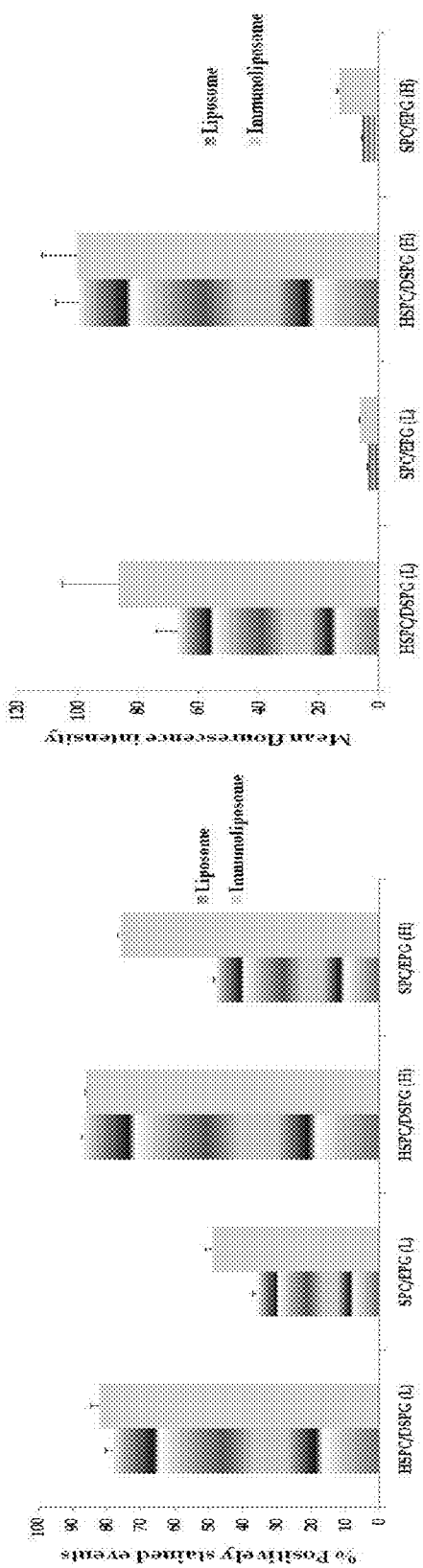
FIG. 7 illustrates the comparison of liposomal and immunoliposomal formulations in terms of uptake rate by J774.A1 macrophages, as set forth hereinabove in connection with FIGS. 5 and 6, but following 24 hours of incubation pursuant to the teachings of the present invention. The results are shown as % positively stained events (left) and mean fluorescence intensity (right) according to flow cytometric data. H: high dose (final phospholipid concentration in each well was set at 0.1 mM); L (final phospholipid concentration in each well was set at 0.2 mM). Values are expressed as mean±SEM, n=3.

The uptake of HSPC/DSPG liposomes and their correspondent immunoliposomes were generally augmented at the higher tested concentration, as illustrated and described in more detail in the charts set forth in FIG. 5, FIG. 6 and FIG. 7 of the DRAWINGS, respectively. Conjugation of liposomes with apo B-100 monoclonal antibody was not associated with a marked change in the uptake rate of nanoparticles by J774.A1 macrophages, as also illustrated and described in more detail in the charts set forth in FIG. 5, FIG. 6 and FIG. 7 of the DRAWINGS, respectively.

In-Vivo Hypolipidemic Assay

Male albino mice (20-30 g) were used for in-vivo experiments. The animals were housed in constant room temperature (23-25° C.), kept in plastic cages (47×34×18 cm3) with sawdust and had free access to food and water. Mice were starved for ~6 hours prior to experiment. For the screening tests, animals were randomly divided into 11 groups of four mice each. Hyperlipidemia was induced in all groups via injection of a single dose of tyloxapol (Triton WR-1339) at a dose of 300 mg/kg mouse weight. Simvastatin (80 mg/kg) and saline were used as positive and negative control, respectively. Liposomal formulations were intravenously injected through a tail vein at a dose of 200 µmole phospholipid/kg. Blood collection was performed 1 hour post-injection via cardiac puncture, following anesthesia with ketamine/xylazine combination. Dose-dependent experiments were conducted with the same protocol using 3 doses of 200 µmole/kg, 100 µmole/kg and 50 µmole/kg.

In Vivo Lipid-Lowering Activity

Figure 8:
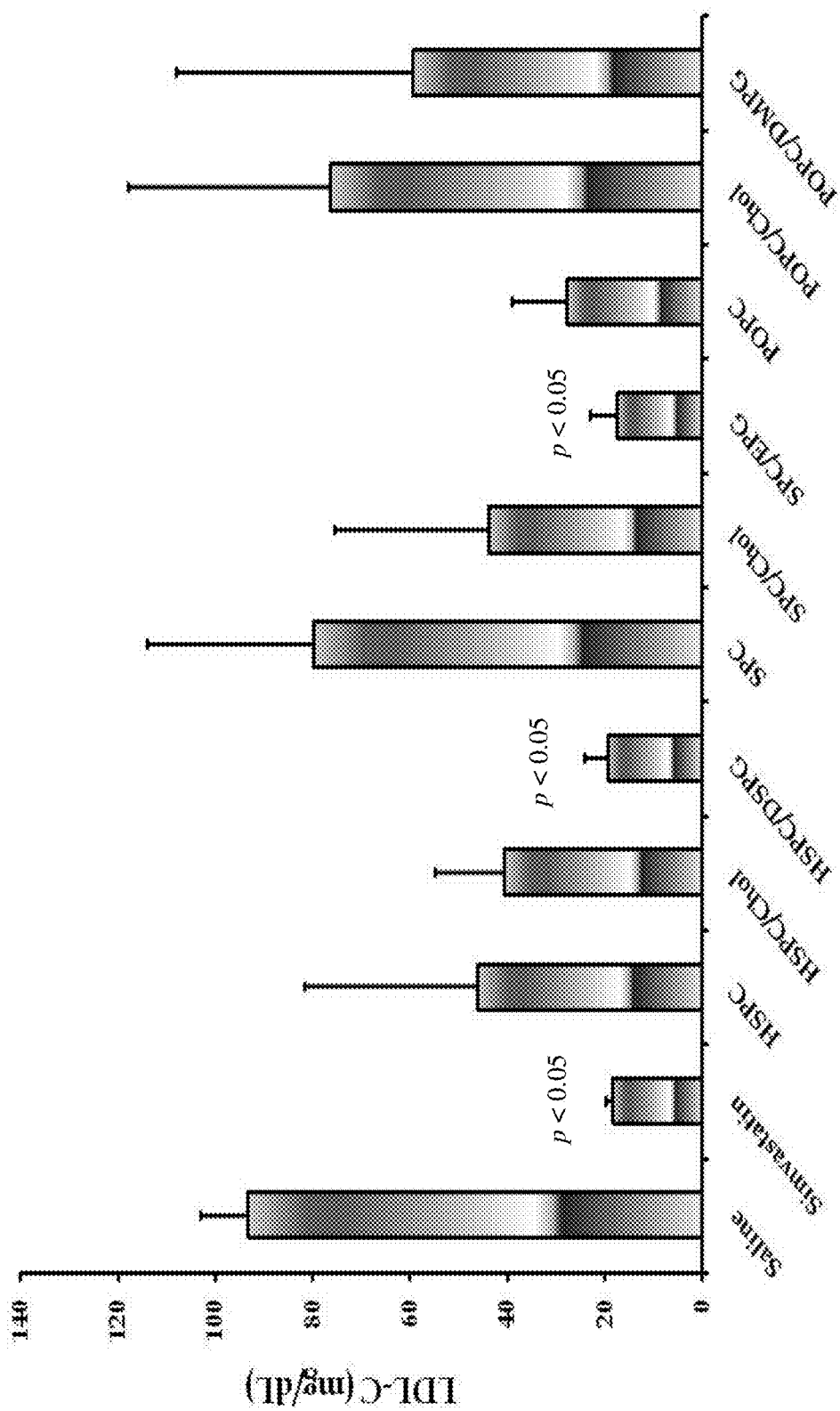
FIG. 8 illustrates in-vivo screening of liposomal different liposomal formulations for their effect on serum LDL-C concentrations pursuant to further teachings of the present invention. As before, the values are expressed as mean±SEM.
Figure 9:
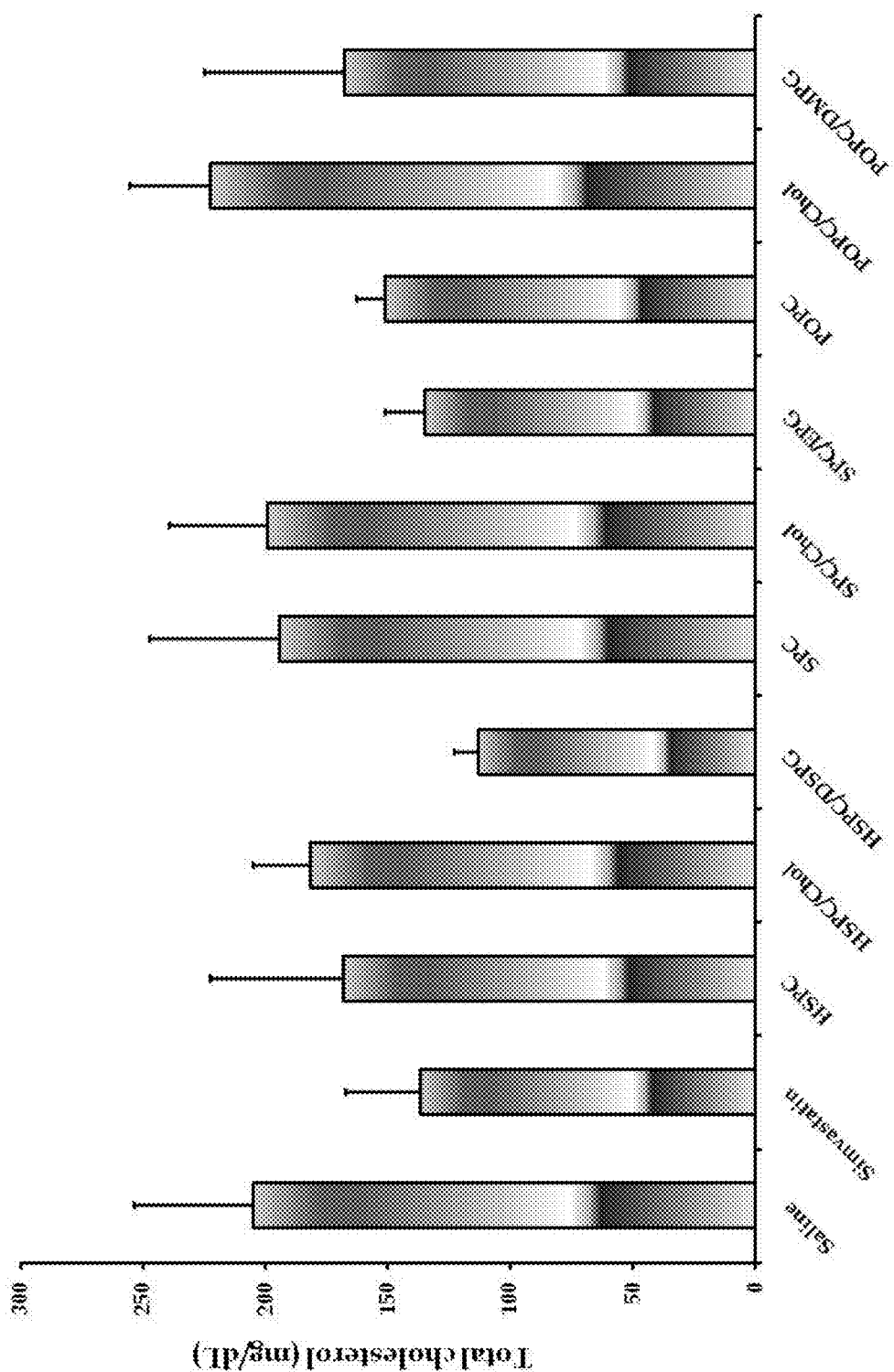
FIG. 9 illustrates in-vivo screening of liposomal different liposomal formulations for their effect on serum total cholesterol concentrations pursuant to the teachings of the present invention. Values are expressed as mean±SEM.

Prepared formulations were initially screened for their anti-dyslipidemic activity. Among the 9 tested formulations, the most brilliant effects on serum LDL-C, as illustrated and described in more detail in the charts set forth in FIG. 8 of the DRAWINGS, and total cholesterol, as illustrated and described in more detail in the charts set forth in FIG. 9 of the DRAWINGS, were from HSPC/DSPG and SPC/EPG, both having a net negative charge. The anti-dyslipidemic activity of these two formulations was significantly ($p<0.05$) more than other formulations. As shown, there were no significant differences in the anti-dyslipidemic activity of these two formulations with simvastatin. Based on the aforesaid screening tests, these 2 formulations were selected and further evaluated for their dose-dependent anti-dyslipidemic effects, as described further hereinbelow.

Lipoprotein Measurements

After being allowed to clot at room temperature, collected blood was centrifuged at 14000 rpm for 10 min to obtain serum. A complete lipid profile for LDL-C, HDL-C, total cholesterol and triglycerides was determined in serum samples. Lipoprotein measurements were performed based on the routine enzymatic methods using commercial kits. An atherogenic index was calculated using two routinely-used equations i.d. LDL/HDL ($AI_1$) and log (triglycerides/HDL-C) ($AI_2$), as are understood in the art.

Cytotoxicity Assessment

Cytotoxicity of nanoliposomes was assessed using Alamar Blue.® J774.A1 cells were seeded in 96-well plates, allowed to adhere and grow for an overnight at 37° C. and 5% $CO_2$, and then used in the cytotoxicity experiment. A total of three doses (5, 10 and 15 µL of the 20 mM liposomal preparation); and three different time points (3, 12 and 24 hours) were used to determine cytotoxicity of the nanoliposomes. Alamar Blue® solution was directly added to the medium resulting in a final concentration of 10% in each well. After 4 hours of incubation with Alamar Blue,® the absorbance was read at 545 nm using a microplate reader according to the manufacturer leaflet.

Statistical Analysis

Statistical analyses of the data accumulated in the aforementioned assessments are preferably performed using Statistical Package for the Social Sciences (SPSS) software. The values, as above, were expressed as mean±SEM. Between-group comparisons of serum LDL-C and macrophage uptake measures were performed using one-way analysis of variance (ANOVA) statistical models with a Tukey-Kramar test for post-hoc multiple comparisons. A two-sided p-value of <0.05 was considered as statistically significant.

Example 1: Dose-Dependent Experiments of Liposomes

LDL-C

Figure 10:
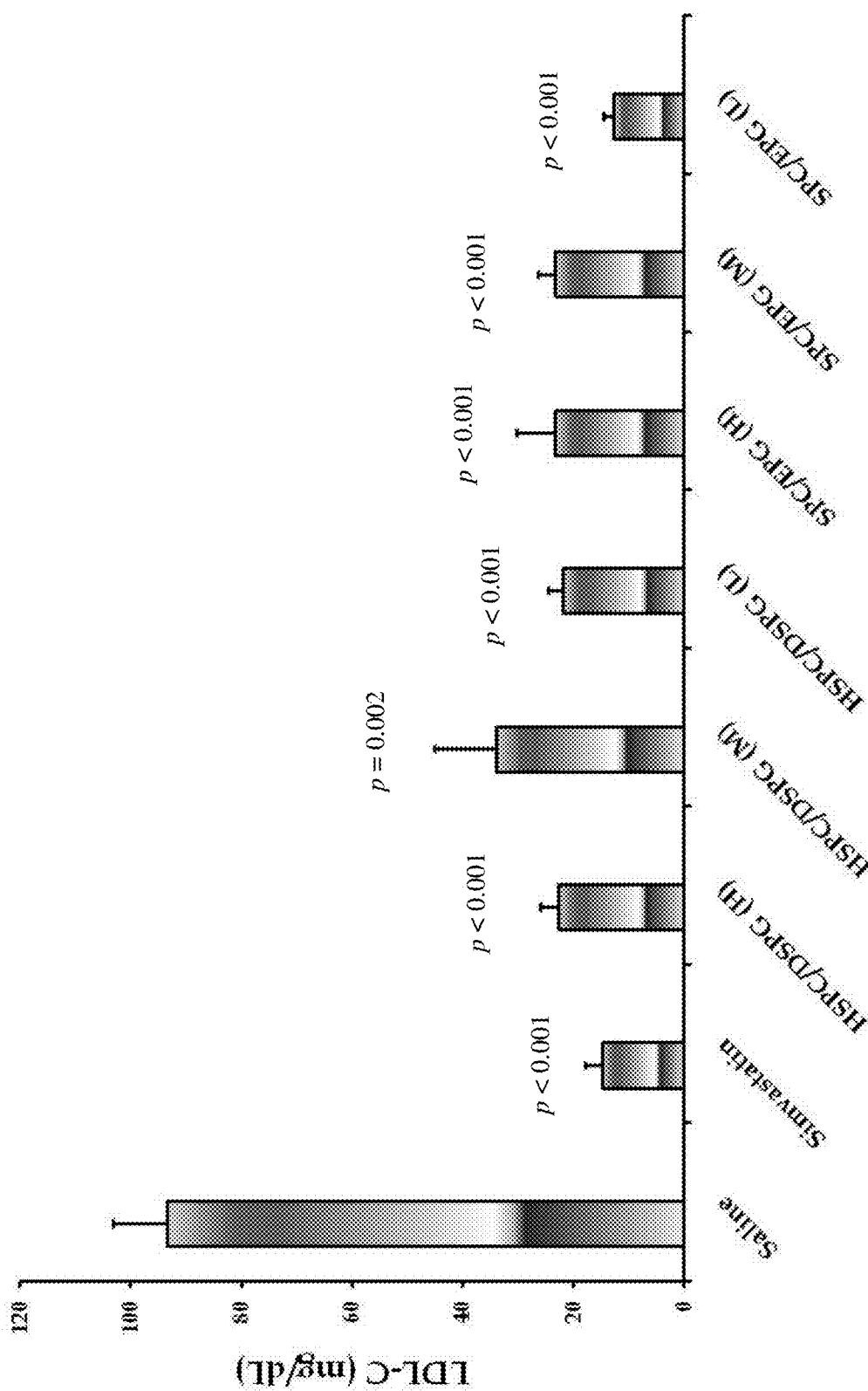
FIG. 10 illustrates in-vivo effects of different doses of anionic liposomes on serum LDL-C concentrations pursuant to still further teachings of the present invention. H: high concentration (200 μmole/kg); M: medium concentration (100 mole/kg); L: low concentration (50 μmole/kg). Values are expressed as mean±SEM.

SPC/EPG and HSPC/DSPG formulations showed a brilliant LDL-lowering capacity at all tested doses: high (H), medium (M) and low (L). The magnitude of effects were in the following order: SPC/EPG (L)>simvastatin>HSPC/DSPG (L)>HSPC/DSPG (H)>SPC/EPG (M)=SPC/EPG (H)>HSPC/DSPG (M), as illustrated and described in more detail in the charts set forth in FIG. 10 of the DRAWINGS.

Figure 11:
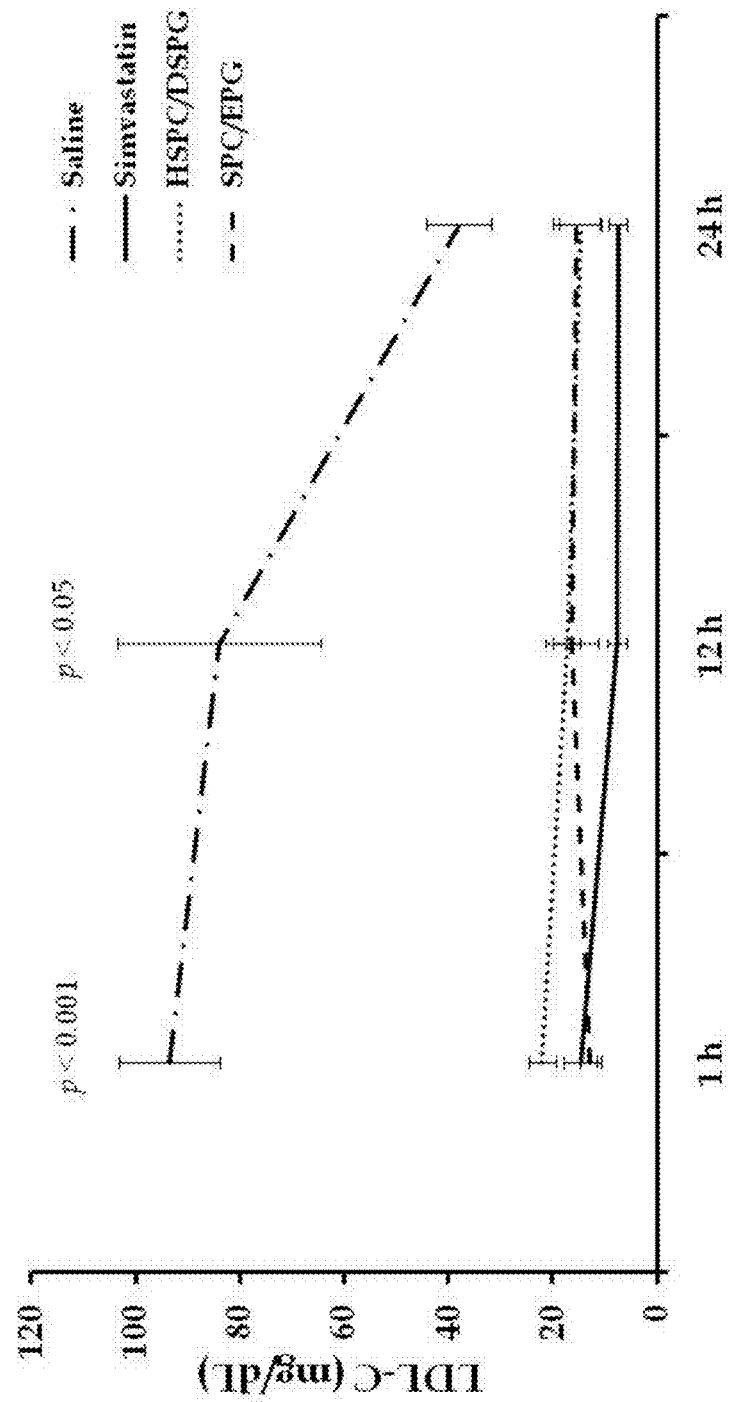
FIG. 11 illustrates in-vivo effects of anionic liposomes (50 μmole/kg) on serum LDL-C concentrations at different time points pursuant to the teachings of the present invention. P-values refer to the statistical comparison of liposomal preparations and simvastatin with saline. As also described in more detail hereinbelow, no significant difference was found between liposomal preparations and simvastatin.

As low-doses of liposomal preparations showed efficacy in the in vivo model, they were further tested for LDL-C lowering activity at 12 h and 24 hour post-injection, as well. The results indicated that reduced LDL-C levels following liposome injection are sustained at 12 hour and 24 hour time points, with no significant difference compared to those achieved at the 1 hour time point post-injection, as illustrated and described in more detail in the charts set forth in FIG. 11 of the DRAWINGS.

Total Cholesterol

Figure 12:
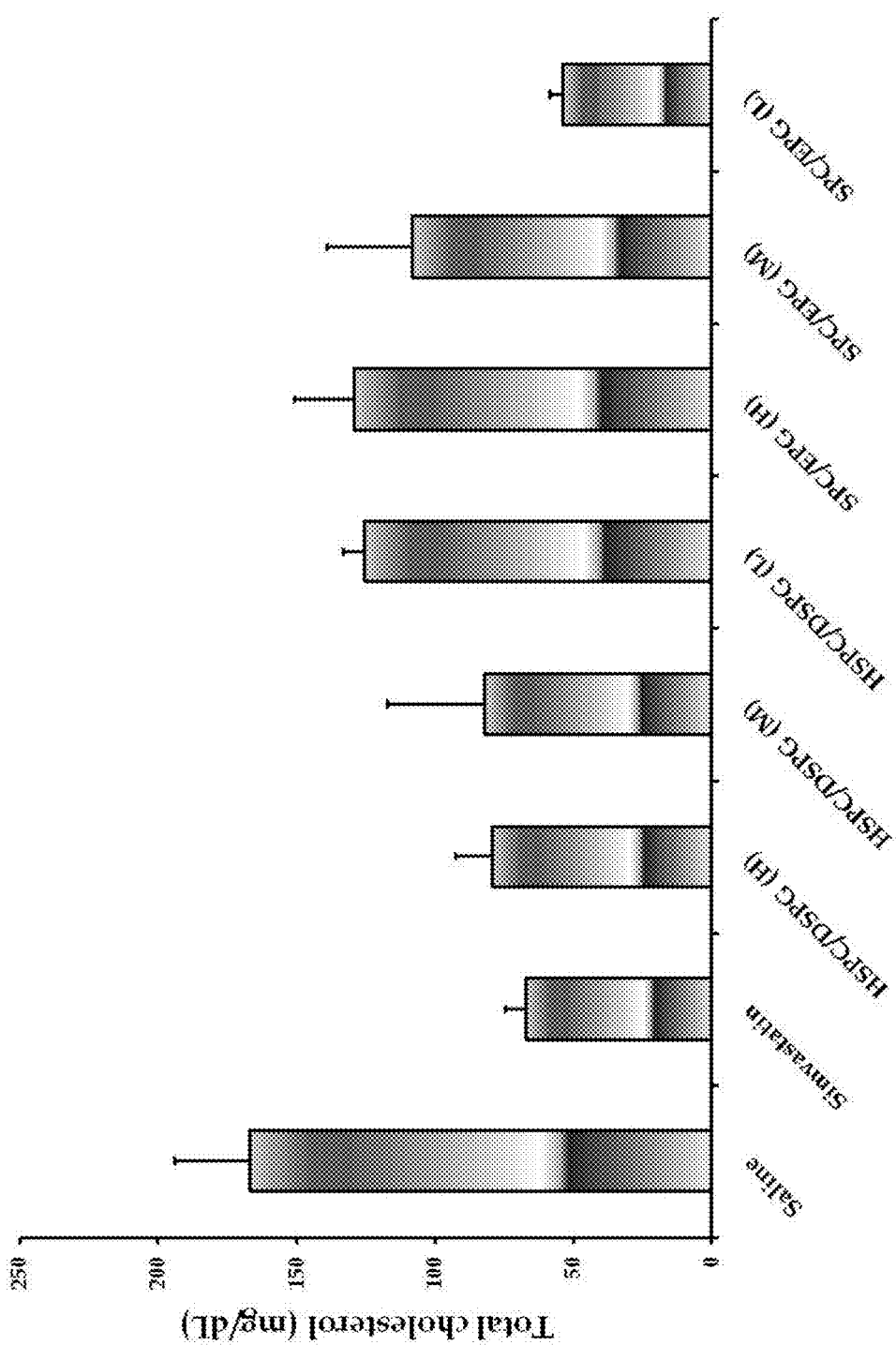
FIG. 12 illustrates in-vivo effects of different doses of anionic liposomes on serum total cholesterol concentrations pursuant to other teachings of the present invention. H: high concentration (200 μmole/kg); M: medium concentration (100 mole/kg); L: low concentration (50 μmole/kg). Values are expressed as mean±SEM.

As found and as illustrated, all doses of tested liposomal formulations reduced serum total cholesterol levels. The magnitude of effects were in the following order: SPC/EPG (L)>simvastatin>HSPC/DSPG (H)>HSPC/DSPG (M)>SPC/EPG (M)>HSPC/DSPG (L)>SPC/EPG (H), as illustrated and described in more detail in the charts set forth in FIG. 12 of the DRAWINGS.

HDL-C

Figure 13:
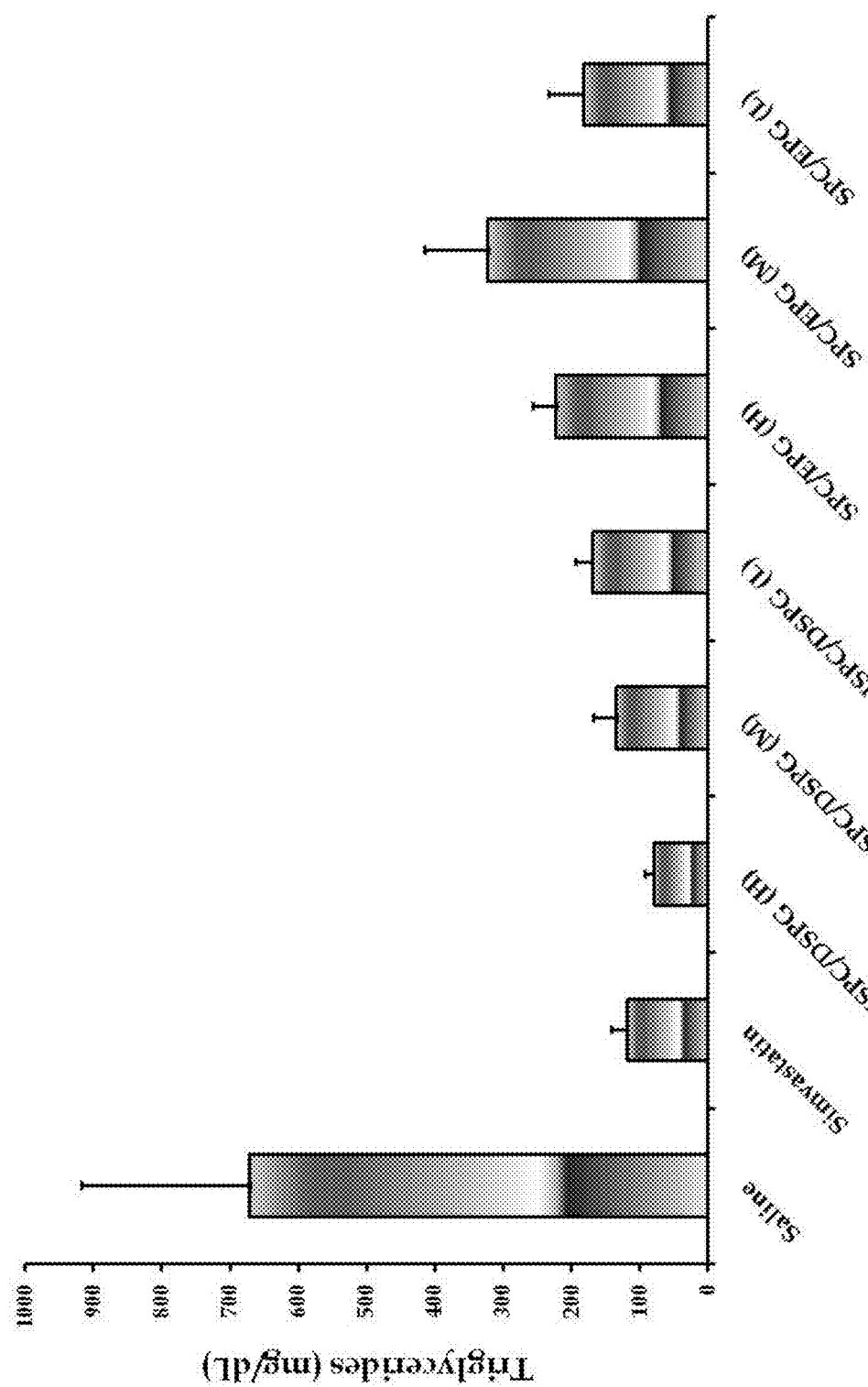
FIG. 13 illustrates In-vivo effects of different doses of anionic liposomes on serum triglycerides concentrations pursuant to the teachings of the present invention. H: high concentration (200 μmole/kg); M: medium concentration (100 μmole/kg); L: low concentration (50 μmole/kg). Values are expressed as mean±SEM.

Promising elevations of serum HDL-C was observed following administration of liposomes. For some formulations, these elevations were greater than that of simvastatin. The order of HDL-C boosting effect was: HSPC/DSPG (L)>SPC/EPG (H)>HSPC/DSPG (H)>simvastatin>HSPC/DSPG (M)>SPC/EPG (M)>SPC/EPG (L), as illustrated and described in more detail in the charts set forth in FIG. 13 of the DRAWINGS.

Triglycerides

Figure 14:
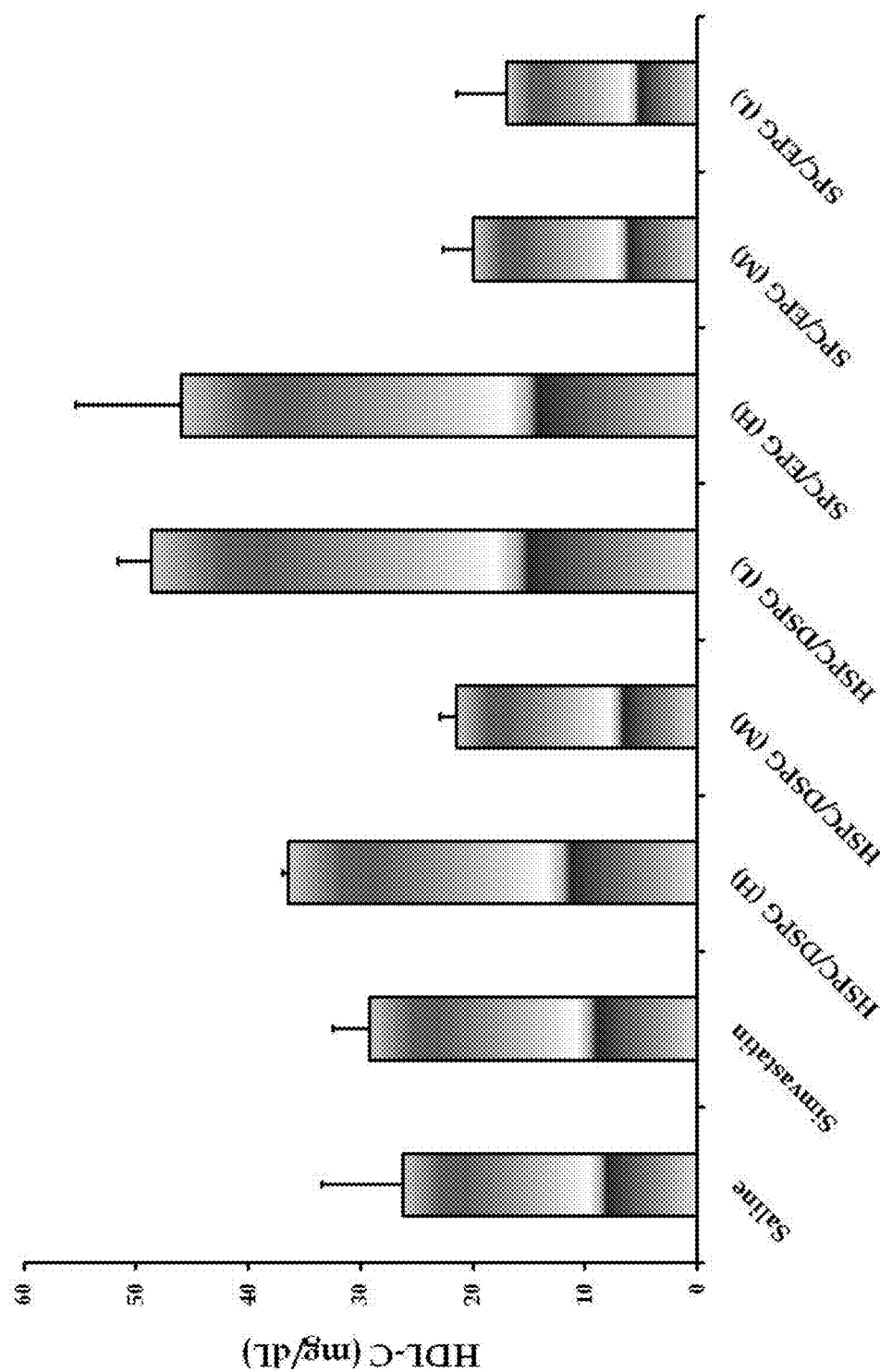
FIG. 14 illustrates in-vivo effects of different doses of anionic liposomes on serum HDL-C concentrations pursuant to further teachings of the present invention. H: high concentration (200 μmole/kg); M: medium concentration (100 μmole/kg); L: low concentration (50 μmole/kg). Values are expressed as mean±SEM.

Marked reduction of serum triglycerides were observed following administration of nanoliposomes, with the following order: HSPC/DSPG (H)>simvastatin>HSPC/DSPG (M)>HSPC/DSPG (L)>SPC/EPG (L)>SPC/SPG (H)>SPC/EPG (M), as illustrated and described in more detail in the charts set forth in FIG. 14 of the DRAWINGS.

Atherogenic Indexes

Figure 15:
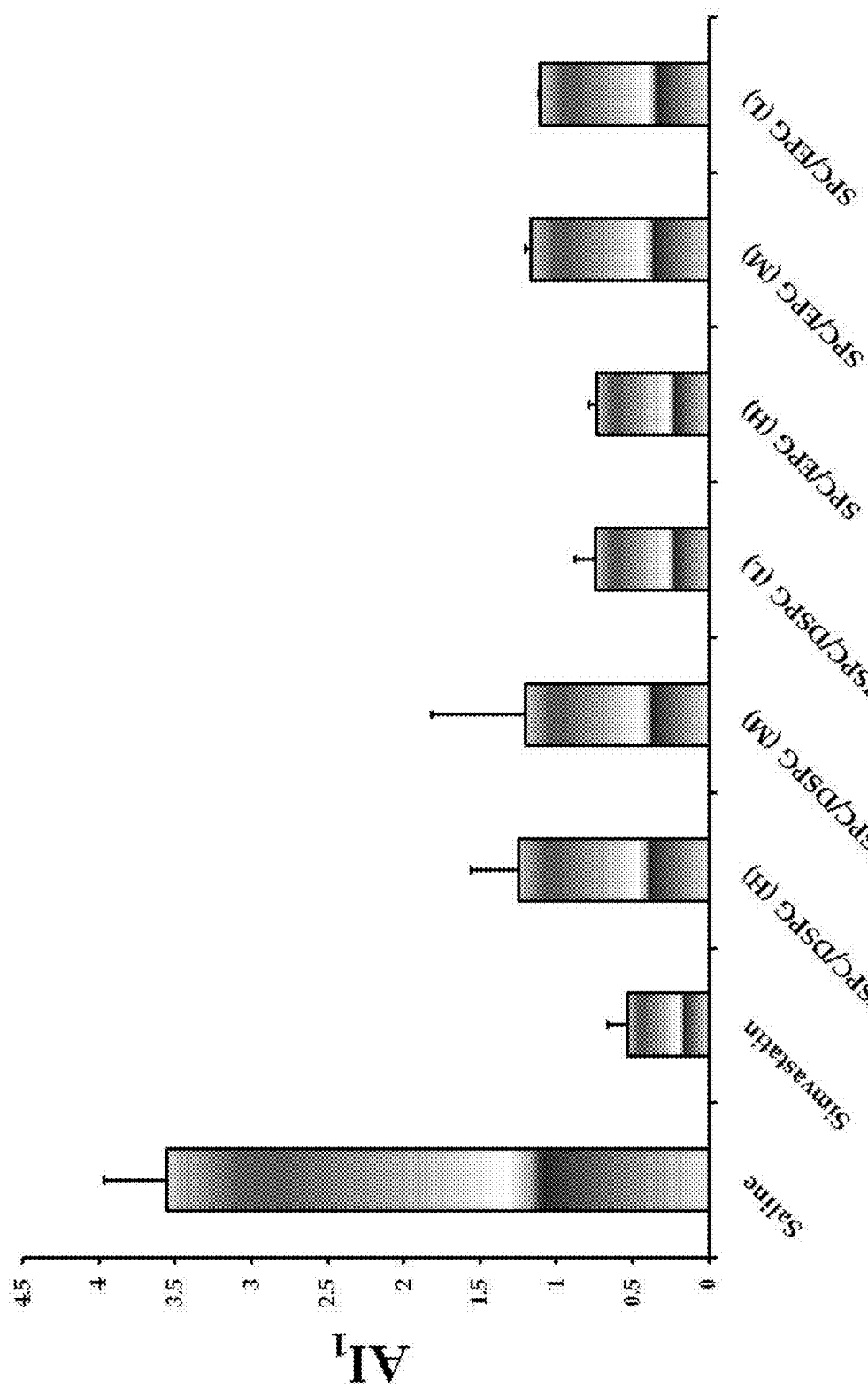
FIG. 15 illustrates in-vivo effects of different doses of anionic liposomes on $AI_1$ calculated as LDL-C/HDL-C pursuant to still further teachings of the present invention. AI: atherogenic index. H: high concentration (200 μmole/ kg); M: medium concentration (100 μmole/kg); L: low concentration (50 μmole/kg). Values are expressed as mean±SEM.

The overall impact of tested formulations on the cardiovascular risk was assessed by calculating atherogenic indexes $AI_1$ and $AI_2$. For $AI_1$, the efficacy of treatments decreased in the following order: simvastatin>SPC/EPG (H)>HSPC/DSPG (L)>SPC/EPG (L)>SPC/EPG (M)>HSPC/DSPG (M)>HSPC/DSPG (H), as illustrated and described in more detail in the charts set forth in FIG. 15 of the DRAWINGS. With respect to $AI_2$, the efficacy of formulations decreased as follows: HSPC/DSPG (H)>HSPC/DSPG (L)>simvastatin>SPC/EPG (H)>HSPC/DSPG (M)>SPC/EPG (L)>SPC/EPG (M), as illustrated and described in more detail in the charts set forth in FIG. 16 of the DRAWINGS.

Example 2: Dose-Dependent Experiments of Immunoliposomes

LDL-C

SPC/EPG and HSPC/DSPG immunoliposomes showed a brilliant LDL-C lowering capacity at all tested doses. The magnitude of effects were in the following order: imlip HSPC/DSPG (L)>imlip HSPC/DSPG (M) imlip HSPC/DSPG (H)>simvastatin>SPC/EPG (L)>SPC/EPG (H)>SPC/EPG (M), as illustrated and described in more detail in the charts set forth in FIG. 17 of the DRAWINGS.

Total Cholesterol

Immunoliposomes prepared from HSPC/DSPG liposomes were markedly more active than those prepared from SPC/EPG liposomes. The magnitude of effects were in the following order: imlip HSPC/DSPG (M)>simvastatin>imlip HSPC/DSPG (H)>imlip HSPC/DSPG (L)>imlip SPC/EPG (L)>imlip SPC/EPG (H)>imlip SPC/EPG (M), as illustrated and described in more detail in the charts set forth in FIG. 18 of the DRAWINGS.

HDL-C

Promising elevations of serum HDL-C was observed following administration of immunoliposomes. For some formulations, these elevations were greater than that of simvastatin. The order of HDL-C boosting effect was: imlip SPC/EPG (L)>imlip SPC/EPG (H)>imlip SPC/EPG (M)>imlip HSPC/DSPG (L)>imlip HSPC/DSPG (H)>simvastatin>imlip HSPC/DSPG (M), as illustrated and described in more detail in the charts set forth in FIG. 19 of the DRAWINGS.

Triglycerides

Marked reduction of serum triglycerides were observed following administration of immunoliposomes, with the following order: imlip HSPC/DSPG (M)>imlip HSPC/DSPG (L)>imlip HSPC/DSPG (H)>imlip SPC/EPG (L)>simvastatin>imlip SPC/SPG (H)>imlip SPC/EPG (M), as illustrated and described in more detail in the charts set forth in FIG. 20 of the DRAWINGS.

Atherogenic Indexes

For AI1, the efficacy of treatments decreased in the following order: imlip HSPC/DSPG (L)>imlip SPC/EPG (L)>simvastatin>imlip SPC/EPG (H)>imlip HSPC/DSPG (H)>imlip SPC/EPG (M)>imlip HSPC/DSPG (M) (FIG. 21). With respect to AI2, the efficacy of formulations decreased as follows: imlip HSPC/DSPG (L)>imlip SPC/EPG (L)>imlip HSPC/DSPG (H)>imlip SPC/EPG (H)>simvastatin>imlip SPC/EPG (M)>imlip HSPC/DSPG (M), as illustrated and described in more detail in the charts set forth in FIG. 22 of the DRAWINGS.

Cytotoxicity Assays

Finally, cytotoxicity of the HSPC/DSPG and SPC/EPG formulations were dose- and time-dependently evaluated using Alamar Blue® assay. Several doses (5, 10 and 15 μL) were used, and cell viability was determined after 3, 12 and 24 hours of incubation. Overall, the viability of cultured macrophages was almost completely maintained in the presence of both tested liposomal preparations regardless of dose and duration of incubation. The results of the various cytotoxicity assays are summarized and illustrated in more detail in the charts set forth in FIG. 23 and FIG. 24 of the DRAWINGS, respectively.

CONCLUSION

In the in vitro uptake assays, liposomes containing anionic phospholipids demonstrated a higher rate of uptake by macrophages. This is well within expectations, as liposomes containing high (>75%) contents of PG have been previously shown to interact and coalesce with LDL particles. The resulting particles might then bind to an LDL receptor via their apolipoprotein B-100 component. It has been demonstrated that such liposome/LDL complexes, upon formation, are phagocytosed by macrophages. In addition, an electrostatic interaction has also been shown between liposomes containing 50% anionic phospholipids and cationic residues in apo B-100. Several lines of evidence have also indicated that anionic phospholipids are actively uptaken by cells, in particular macrophages, via SRBI scavenger receptors or CD36.

Further, intravenous administration of phosphatidylinositol vesicles causes a significant induction of reverse cholesterol transport (RCT) and a striking increase in free cholesterol clearance from plasma. This phenomenon was found to be due to the increase in the surface potential of lipoproteins, in particular HDL, which is itself secondary to the incorporation of anionic phospholipids into the lipoproteins.

Following internalization, liposomes will be targeted to lysosomes where they will be further metabolized. The accumulation of nanoliposome/LDL complexes in the hepatic tissue and their degradation by lysosomes represent an elimination route very similar to that which naturally occurs for LDL. Therefore, the liposomal anti-dyslipidemic approach of the present invention described herein is virtually or substantially a mimic of the body's natural mechanism.

In the in vivo assays, SPC/EPG and HSPC/DSPG formulations exhibited high LDL-lowering activity, which was elicited as early as 1 hour post-injection and sustained for at least 24 hours. The effects of these two formulations were even comparable to those of simvastatin, used as the standard anti-dyslipidemic compound. Conjugation of liposomes with apo B-100 monoclonal antibodies increased the LDL-C loweirng activity of HSPC/DSPG but not SPC/EPG formulation. However, both of the immunoliposomal formulations caused a greater reduction in the $AI_1$ and $AI_2$, leading to the overall cardiovascular benefit beyond what is achieved by corresponding liposomal formulations.

Simvastatin was administered via parenteral route in order to exert higher efficacy. For routine clinical practice, preparation of a parenteral dosage form of simvastatin is a great challenge as the drug is poorly water soluble. Hence, the lipid lowering effects observed from parenteral simvastatin (solubilized in dimethylsulfoxide) would certainly not be achieved by oral dosage forms in the routine clinical practice. In contrast, parenteral dosage forms of liposomes in aqueous vehicles could be easily developed regarding the amphiphilic nature of phospholipids. Hypolipidemic effects become more attractive when considering that most of the currently-available, lipid-lowering medications, such as fibrates, bile acid sequestrants and niacin, cannot reach the same efficacy.

Along with the promising magnitude of positive effects, as set forth and described hereinabove, another issue that deserves attention is the rapid effect of the liposomal formulations pursuant to the teachings of the present invention. In connection with a study related to the instant invention, blood samples were collected around 1 hour following induction of hyperlipidemia. Such rapid-acting hypolipidemic agents are especially helpful in the management of homozygous familial hypercholesterolemia (HFH) patients, who have very high levels of LDL-C (due to mutations in the LDL receptor gene) and develop premature CVD at the age of 30-40. While these patients do not respond to statin therapy, their management is limited to LDL apheresis, which is an unpleasant, costly and non-available method. It seems plausible that higher doses of the lisposomal formulations described in the present invention could rapidly and effectively reduce serum LDL levels in these patients with HFH, offering a further benefit of the compositions, techniques and methods of the instant invention, as described herein.

Another important finding was the remarkable effects of nanoliposomes on serum HDL-C concentrations. Apart from increasing HDL concentration, liposomes can enhance the function of HDL through interacting with lipoprotein in remodeling and shuttling processes, both of which deplete cholesterol content of HDL and thus making it a better acceptor of subendothelial cholesterol. Owing to the established inverse association between serum HDL-C and CVD risk, there has been a surge of interest in developing strategies to raise HDL-C levels. However, statins, as noted, have only moderate and non-clinically relevant effects on HDL-C, which is usually considered as a drawback for this class of drugs. Hence, anionic liposomes may be regarded as potential anti-dyslipidemic agents that could simultaneously affect both LDL-C and HDL-C. Furthermore, boosting HDL-C, along with reduction of serum triglycerides, may pose a possible benefit for the use of anionic liposomes for the management of metabolic syndrome and related disorders including non-alcoholic fatty liver disease for which hypertriglyceridemia and reduced HDL-C are important risk factors, offering additional benefits in the use of the present invention.

The overall cardioprotective effect of a formulation could be assessed by calculating the AI. In the present invention, a promising impact of the HSPC/DSPG formulation was observed on both $AI_1$ and $AI_2$. These effects were greater than those exerted by SPC/EPG. It might be speculated that the higher activity of HSPC/DSPG liposomes is due to their higher Tm value, which makes the resulting liposome/LDL complexes more stable. Consequently, such complexes would have longer availability and accessibility to kupffer cells in the liver, and hence more efficiently uptaken, offerin yet more benefits from the compositions, techniques, methods and principles of the present invention, as described herein.

In summary, the findings of the instant invention and associated study indicate that empty, cholesterol-free nanoliposomal formulations containing 70-80% anionic phospholipid (PG) serve as safe, effective, rapid acting, inexpensive, biocompatible and biodegradable anti-dyslipidemic agents. Future investigations on the clinical efficacy and further characterization of the magnitude of LDL-lowering effects of these formulations, particularly in other models of dietary and genetically induced hyperlipidemia, are warranted and may uncover further innovations.

Additionally, HSPC/DSPG and SPC/EPG liposomes had the best anti-dyslipidemic activity. These two formulations had a favorable impact on all lipid profile parameters (LDL-C, HDL-C, total cholesterol and triglycerides) at all the tested doses. As noted, there beneficial effects reduced LDL-C levels, which were sustained for at least 24 hours. Atherogenic indices (either calculated as LDL-C/HDL-C or log (triglycerides/HDL-C) were also effectively reduced following HSPC/DSPG and SPC/EPG injections. Targeting of HSPC/DSPG and SPC/EPG liposomes against apo B-100 component of LDL increased, increased their LDL-lowering effects.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the breadth or scope of the applicant's concept. Furthermore, although the present invention has been described in connection with a number of exemplary embodiments and implementations, the present invention is not so limited but rather covers various modifications and equivalent arrangements, which fall within the purview of the appended claims.

What is claimed is:

1. A targeted liposomal composition comprising:
a nanoliposomal composition; and
at least one antibody, the at least one antibody comprising an apolipoprotein antibody,
wherein;
the nanoliposomal composition comprises at least one anionic phospholipid and at least one neutral phospholipid, the at least one anionic phospholipid being present with an amount of between 50 to 90 weight percentage of the targeted liposomal composition,
the at least one antibody is conjugated within the nanoliposomal composition, and
the targeted liposomal composition does not include cholesterol.

2. The targeted liposomal composition according to claim 1, wherein an average diameter of one or more liposomal particles present in said targeted liposomal composition is within a range of about 90-150 nanometers.

3. The targeted liposomal composition according to claim 1, wherein the at least one anionic phospholipid comprises from about 65 to about 85 weight percent of the targeted liposomal composition.

4. The targeted liposomal composition according to claim 1, wherein the at least one neutral phospholipid is selected from the group consisting of Hydrogenated Soy Phosphatidylcholine (HSPC), Soy Phosphatidylcholine (SPC) and combinations thereof.

5. The targeted liposomal composition according to claim 1, wherein the at least one anionic phospholipid is egg phosphatidylglycerol (EPG).

6. The targeted liposomal composition according to claim 1, wherein the at least one anionic phospholipid is Distearoyl Phosphatidylglycerol (DSPG).

7. The targeted liposomal composition according to claim 1, wherein said Apolipoprotein antibody comprises an Apolipoprotein B 100 antibody.

8. The targeted liposomal corn position according to claim 5, said at least one neutral phospholipid is Soy Phosphatidylcholine (SPC).

9. The targeted liposomal composition according to claim 8, wherein the ratio of SPC to EPG in said liposomal composition is about 1:3.

10. The targeted liposomal composition according to claim 6, wherein said at least one neutral phospholipid is Hydrogenated Soy Phosphatidylcholine (HSPC).

11. The targeted liposomal composition according to claim 10, wherein the ratio of HSPC to DSPG in said liposomal composition is about 1:3.

12. The targeted liposomal composition according to claim 1, wherein said at least one anionic phospholipid is selected from the group consisting of egg phosphatidylglycerol (EPG), Distearoyl Phosphatidylglycerol (DSPG) and combinations thereof.

* * * * *